(12) United States Patent
Narayan et al.

(10) Patent No.: US 9,517,244 B2
(45) Date of Patent: Dec. 13, 2016

(54) THERAPEUTIC COMBINATIONS FOR USE IN NEOPLASIA

(75) Inventors: Satya Narayan, Gainesville, FL (US); Aruna S. Jaiswal, Gainesville, FL (US); David A. Ostrov, Gainesville, FL (US); Sukwon Hong, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 90 days.

(21) Appl. No.: 14/113,365

(22) PCT Filed: Apr. 20, 2012

(86) PCT No.: PCT/US2012/034491
§ 371 (c)(1),
(2), (4) Date: Jan. 28, 2014

(87) PCT Pub. No.: WO2012/145653
PCT Pub. Date: Oct. 26, 2012

(65) Prior Publication Data
US 2014/0134275 A1    May 15, 2014

Related U.S. Application Data

(60) Provisional application No. 61/478,241, filed on Apr. 22, 2011.

(51) Int. Cl.
| | | |
|---|---|---|
| *A61K 31/282* | (2006.01) | |
| *A61K 31/529* | (2006.01) | |
| *A61K 31/53* | (2006.01) | |
| *A61K 31/7068* | (2006.01) | |
| *A61K 45/06* | (2006.01) | |
| *A61K 31/7088* | (2006.01) | |
| *A61K 31/495* | (2006.01) | |
| *A61K 33/24* | (2006.01) | |

(52) U.S. Cl.
CPC ......... *A61K 31/7068* (2013.01); *A61K 31/282* (2013.01); *A61K 31/495* (2013.01); *A61K 31/53* (2013.01); *A61K 31/7088* (2013.01); *A61K 33/24* (2013.01); *A61K 45/06* (2013.01)

(58) Field of Classification Search
None
See application file for complete search history.

(56) References Cited

U.S. PATENT DOCUMENTS

2010/0285008 A1    11/2010   Kelley

OTHER PUBLICATIONS

Yang et al. ("Yang", Molecular Cancer Therapeutics, 2005, 1923-1935).*
Heinemann et al ("Heinemann", Annals of Oncology, 2000, 11, 1399-1403).*
Sung Yang et al. 'Alternations in the Expression of the Apurinic/Apyrimidinic Endonuclease-1/Redox Factor-1 (APE/Ref-1) in Human Melanoma and Identification of the Therapeutic Potential of Resveratrol as an APE/Ref-1 Inhibitor', Molecular Cancer Therapeutics, 2005, vol. 4, No. 12, pp. 1923-1935 ISSN: 1535-7163.
Dong Wang et al., 'PE1 Overexpression is Associated with Cisplatin Resistance in Non-small Cell Lung Cancer and Targeted Inhibition of APE1 Enhances the Activity of Cisplatin in A549 Cells', Lung Cancer, 2009, vol. 66. No. 3, pp. 298-304, ISSN: 0169-5002.
Zvi Symon et al., 'Concurrent Chemoradiotherapy With Gemcitabine and Cisplatin for Pancreatic Cancer: From the Laboratory to the Clinic', Int. J. Radiation Oncology Biol. Phys., 2002, vol. 53, No. 1, pp. 140-145, ISSN: 0360-3016.
JP Lau et al, 'Effects of Gemcitabine on APE/Ref-1 Endonuclease Activity in Pancreatic Cancer Cells, and the Therapeutic Potential of Antisense Oligonucleotides', British Journal of Cancer, 2004, vol. 91, No. 6, pp. 1166-1173, ISSN: 0007-0920.
International Search Report of PCT/US2012/034491.

* cited by examiner

*Primary Examiner* — Misook Yu
*Assistant Examiner* — Kauser Akhoon
(74) *Attorney, Agent, or Firm* — Wolf, Greenfield & Sacks, P.C.

(57) ABSTRACT

The invention features compositions and methods that are useful for the treatment of neoplasia (e.g., pancreatic cancer, colon cancer, brain cancer) by increasing DNA damage, reducing nucleotide synthesis, and reducing base excision repair (BER).

6 Claims, 15 Drawing Sheets

A

Chemical structure of NSC-30049 {1-(4-Chloro-2-butenyl)-1.lambda.~5~,3,5,7-tetraazatricyclo[3.3.1.1~3,7~]decane)}

B

NSC 30049

(A)     (B) SAR study plan
1) X = F, Cl, Br, OH     2) olefin = *trans* or *cis*
3) NR₃ =

R = H, Me, Et

A

B

A. Protocol

B. Tumor volume

A. Viability of U87MG cancer-initiating cells

B. Vaibility of GBM-L0 cancer-initiating cells

| TMZ (μM) | 0 | 10 | 100 |
| NSC-30049 (μM) | 2.5 | 2.5 | 2.5 |

A. Number of U87MG spheroids

B. U87MG spheroids

APE1

```
  1 mpkrgkkgav aedgdelrte peakksktaa kkndkeaage gpalyedppd ghtspsgkpa
 61 tlkicswnvd glrawikkkg ldwvkeeapd ilclqetkcs enklpaelqe lpglshqyws
121 apsdkegysg vgllsrgcpl kvsygigdee hdqegrviva efdsfvlvta yvpnagrglv
181 rleyrqrwde afrkflkqla srkplvlcgd lnvaheeidl rnpkgnkkna gftpqerqgf
241 gellqavpla dsfrhlypnt pyaytfwtym mnarsknvgw rldyfllshs llpaicdski
301 rskalgsdhc pitlylal
```

THERAPEUTIC COMBINATIONS FOR USE IN NEOPLASIA

CROSS-REFERENCE TO RELATED APPLICATIONS

This application is the U.S. National Stage, pursuant to 35 U.S.C. §371, of U.S. International Application No. PCT/US2012/034491, filed Apr. 20, 2012, designating the United States and published on Oct. 26, 2012 as Publication WO 2012/145653, which claims the benefit of U.S. Provisional Application No. 61/478,241, filed Apr. 22, 2011, the entire contents of which are incorporated herein by reference

BACKGROUND OF THE INVENTION

Pancreatic cancer has the worst prognosis among solid tumors. It is a near fatal disease and one of the most aggressive human malignancies. The management of patients with pancreatic carcinoma depends on the extent of the disease at diagnosis. Surgical resection followed by adjuvant therapy is the standard care for patients diagnosed with early-stage disease. However, the majority of patients present with advanced-stage disease that precludes surgery. Early pancreatic cancer often does not cause symptoms, and the later symptoms are usually nonspecific and varied. Therefore, pancreatic cancer is often not diagnosed until it is advanced. Prognosis for advanced stage patients is extremely poor and the impact of standard therapy is minimal. Currently, gemcitabine along with cisplatin, ephubicin, and 5-fluorouracil, is an active recommended regimen for patients with advanced pancreatic adenocarcinoma. Cisplatin alone is one of the most effective chemotherapeutic agents used for the treatment of variety of cancers including pancreatic cancer. However, the major limitation of the use of high doses to maximize the therapeutic efficacy of cisplatin is restricted due to nephrotoxicity, gastrointestinal toxicity, neurotoxicity, and ototoxicity.

DNA repair pathways have been identified as a potential target for chemotherapeutic intervention of pancreatic cancer, as well as other neoplasias. Normal cells actively repair DNA damage before going into mitosis and avoid DNA damage-induced killing of cells. In contrast, cancer cells possess defective mitotic signals and override the ($G_0/G_1$) check point, but arrest in $G_2/M$ phase and face mitotic catastrophe and death.

At present, no effective treatment exists for pancreatic cancer. New methods of treatment for treating pancreatic cancer and other neoplasias are urgently required.

SUMMARY OF THE INVENTION

The present invention features compositions and methods for enhancing the efficacy of DNA-alkylating drugs for the treatment of neoplasias (e.g., pancreatic cancer, colon cancer, and brain cancers, such as glioblastoma).

In one aspect, the invention provides a method for treating pancreatic cancer in a subject, the method involving administering to said subject an effective amount of an alkylating agent, an agent that binds to ribonucleotide reductase (RR) and reduces nucleotide synthesis relative to a reference, and an agent that binds to Apurinic/apyrimidinic (AP) endonuclease (APE1) and reduces base extension repair relative to a reference, thereby treating the pancreatic cancer.

In another aspect, the invention provides a method for treating pancreatic cancer in a subject, the method involving administering to said subject an effective amount of an alkylating agent, an agent that binds to ribonucleotide reductase (RR) and reduces nucleotide synthesis to a reference, and an agent that binds the endonuclease catalytic domain of APE1, thereby treating pancreatic cancer.

In another aspect, the invention provides a method for treating pancreatic cancer in a subject, the method comprising administering to said subject an effective amount of an alkylating agent, an agent that binds to ribonucleotide reductase (RR) and reduces nucleotide synthesis to a reference, and a chemopreventive agent.

In still another aspect, the invention provides a method for treating a subject having pancreatic cancer, the method involving administering to the subject an effective amount of a pharmaceutical composition containing cisplatin (CIDP), gemeitabine (dFdC), and NSC-30049, thereby treating the subject.

In yet another aspect, the invention provides a method for treating pancreatic cancer in a subject, the method involving administering to the subject a combination of an effective amount of a DNA alkylating agent; a pharmaceutical composition comprising an agent that binds to ribonucleotide reductase (RR) and reduces nucleotide synthesis to a reference; and an agent that binds to Apurinic/apyrimidinic (AP) endonuclease (APE1) and reduces base extension repair relative to a reference, where the administration of the composition reduces the amount of the DNA alkylating agent required to treat the neoplasm, relative to the amount required to treat a neoplasm in a control subject, thereby treating the subject.

In still another aspect, the invention provides a method for treating pancreatic cancer in a subject, the method involving administering to the subject a combination of an effective amount of a DNA alkylating agent; a pharmaceutical composition comprising an agent that binds to ribonucleotide reductase (RR) and reduces nucleotide synthesis to a reference, and NSC-30049 or an analog thereof, where the administration of the composition reduces the amount of the DNA alkylating agent required to treat the neoplasm, relative to the amount required to treat a neoplasm in a control subject, thereby treating the subject.

In another aspect, the invention provides a method of selecting an effective therapy for treating pancreatic cancer in a subject, the method involving identifying the subject as having pancreatic cancer; and administering to the subject an alkylating agent, an agent that binds to ribonucleotide reductase (RR) and reduces nucleotide synthesis to a reference, and an agent that binds to the catalytic domain of APE1 and reduces base extension repair.

In an additional aspect, the invention provides a pharmaceutical composition for the treatment of pancreatic cancer, the composition containing an effective amount of a DNA alkylating agent, an alkylating agent, an agent that binds to ribonucleotide reductase (RR) and reduces nucleotide synthesis relative to a reference, and an agent that binds to Apurinic/apyrimidinic (AP) endonuclease (APE1) and reduces base extension repair relative to a reference.

In another aspect, the invention provides a pharmaceutical composition for the treatment of pancreatic cancer, the composition containing cisplatin (CDDP), gemcitabine (dFdC), and NSC-30049.

In a further aspect, the invention provides a kit for the treatment of a neoplasia, the kit comprising an effective amount of an alkylating agent, an agent that an agent that binds to ribonucleotide reductase (RR) and reduces nucleotide synthesis relative to a reference, NSC-30049, and directions for the use of the kit for the treatment of a neoplasia.

In one aspect, the invention provides a method for treating neoplasia (e.g., pancreatic cancer, colon cancer, brain cancer) in a subject, the method comprising administering to said subject an effective amount of an alkylating agent, and an agent that binds to Apurinic/apyrimidinic (AP) endonuclease (APE1) and reduces base extension repair relative to a reference, thereby treating the neoplasia.

In another aspect, the invention provides a method for treating neoplasia in a subject, the method involving administering to said subject an effective amount of an alkylating agent, and an agent that binds the endonuclease catalytic domain of APE1, thereby treating neoplasia.

In another aspect, the invention provides a method for treating neoplasia in a subject, the method involving administering to said subject an effective amount of an alkylating agent, and a chemopreventive agent.

In still another aspect, the invention provides a method for treating neoplasia in a subject, the method involving administering to the subject a combination containing an effective amount of a DNA alkylating agent and a pharmaceutical composition comprising NSC-30049 or an analog thereof, where the administration of the composition reduces the amount of the DNA alkylating agent required to treat the neoplasm, relative to the amount required to treat a neoplasm in a control subject, thereby treating the subject.

In yet another aspect the invention provides a method of selecting an effective therapy for treating neoplasia in a subject, the method involving identifying the subject as having pancreatic cancer; and administering to the subject an alkylating agent and an agent that binds to the catalytic domain of APE1 and reduces base extension repair.

In an additional aspect, the invention provides a pharmaceutical composition for the treatment of pancreatic cancer, the composition containing an effective amount of a DNA alkylating agent, an alkylating agent and an agent that binds to Apurinic/apyrimidinic (AP) endonuclease (APE1) and reduces base extension repair relative to a reference.

In still another aspect, the invention provides a pharmaceutical composition for the treatment of colon cancer, the composition containing temozolomide and NSC-30049.

In yet another aspect, the invention provides a pharmaceutical composition for the treatment of colon cancer, the composition containing oxaliplatin and NSC-30049.

In still another aspect, the invention provides a pharmaceutical composition for the treatment of brain cancer, the composition containing temozolomide and NSC-30049.

In a further aspect, the invention provides a kit for the treatment of a neoplasia, the kit containing an effective amount of an alkylating agent, NSC-30049, and directions for the use of the kit for the treatment of a neoplasia.

In an additional aspect, the invention provides a method for increasing cytotoxicity of a chemotherapeutic agent in a subject, the method comprising administering to the subject an agent that binds to Apurinic/apyrimidinic (AP) endonuclease (APE1) and reduces base extension repair relative to a reference, and an alkylating agent.

In various embodiments of any of the aspects delineated herein, the agent that binds to APE1 is NSC-30049 or an analog thereof. In various embodiments of any of the aspects delineated herein, the chemopreventive agent is NSC-30049 or an analog thereof. In various embodiments of any of the aspects delineated herein, the APE1 binding site comprises amino acids E96, Y171, D210, N212, F266, W280, L282, and D308, and reduces APE1 endonuclease activity. In various embodiments of any of the aspects delineated herein, the agent that binds to APE1 reduces the activity of the BER pathway relative to a reference.

In various embodiments of any of the aspects delineated herein, the alkylating agent is cisplatin (CIDP), temozolomide, or oxaliplatin. In various embodiments of any of the aspects delineated herein, the method further involves administering an agent that binds to ribonucleotide reductase (RR) and reduces nucleotide synthesis to a reference (e.g., gemcitabine). In various embodiments of any of the aspects delineated herein, the agent that binds RR is gemcitabine (dFdC).

In various embodiments of any of the aspects delineated herein, an effective amount of the combination has reduced toxicity relative to the administration of an effective amount of a DNA alkylating agent alone. In various embodiments of any of the aspects delineated herein, administration of an agent that binds to ribonucleotide reductase (RR) and reduces nucleotide synthesis to a reference and NSC-30049 reduces the amount of an alkylating agent required to treat the pancreatic cancer, relative to the amount required to treat pancreatic cancer in a control subject. In various embodiments of any of the aspects delineated herein, the effective amount of the alkylating agent required to treat the neoplasia when administered in combination with an agent an agent that binds to ribonucleotide reductase (RR) and reduces nucleotide synthesis relative to a reference and NSC-30049 is less than the amount of alkylating agent administered alone.

In various embodiments of any of the aspects delineated herein, the neoplasia is pancreatic cancer, colon cancer, brain cancer. In various embodiments of any of the aspects delineated herein, the neoplasia (e.g., pancreatic cancer, colon cancer, brain cancer) is resistant to conventional chemotherapy.

In another aspect, the invention provides a method for increasing cytotoxicity of a chemotherapeutic agent in a subject, the method involving administering to the subject an agent that binds to Apurinic/apyrimidinic (AP) endonuclease (APE1) and reduces base extension repair relative to a reference, an alkylating agent and an agent that binds to ribonucleotide reductase (RR) and reduces nucleotide synthesis relative to a reference.

In various embodiments of any of the aspects delineated herein, the agent that binds to Apurinic/apyrimidinic (AP) endonuclease (APE1) and reduces base extension repair relative to a reference and the alkylating agent are administered within about 7-14 days. In various embodiments of any of the aspects delineated herein, the agent that binds to Apurinic/apyrimidinic (AP) endonuclease (APE1) and reduces base extension repair relative to a reference and the alkylating agent are administered within about 3-5 days or are administered concurrently.

Other features and advantages of the invention will be apparent from the detailed description, and from the claims.

DEFINITIONS

By "alkylating agent" is meant a cytotoxic agent that transfers an alkyl group to a nucleophilic group on a molecule. Exemplary alkylating agents include, but are not limited to cisplatin, temozolomide, mechlorethamine, cyclophosphamide, chlorambucil, melphalan, ifosfamide, thiotepa, hexamethylmelamine, busulfan, altretamine, procarbazine, dacarbazine carmustine, lomustine, streptozocin, carboplatin, and oxaliplatin.

By "binding to" a molecule is meant having a physicochemical affinity for that molecule.

By "chemopreventive agent" is meant any agent that reduces the risk of neoplasia in a subject having a propensity to develop a neoplasia.

By "computer modeling" is meant the application of a computational program to determine one or more of the following: the location and binding proximity of a ligand to a binding moiety, the occupied space of a bound ligand, the amount of complementary contact surface between a binding moiety and a ligand, the deformation energy of binding of a given ligand to a binding moiety, and some estimate of hydrogen bonding strength, van der Waals interaction, hydrophobic interaction, and/or electrostatic interaction energies between ligand and binding moiety. Computer modeling can also provide comparisons between the features of a model system and a candidate compound. For example, a computer modeling experiment can compare a pharmacophore model of the invention with a candidate compound to assess the fit of the candidate compound with the model.

By "conventional chemotherapeutic agent" is meant one or more chemical agents used in the treatment or control of proliferative diseases, including cancer. Chemotherapeutic agents include cytotoxic and cytostatic agents.

By "Apurinic/apyrimidinic (AP) endonuclease" or "APE1" is meant a polypeptide having at least about 85% identity to NCBI Accession No. P27695, or a fragment thereof having endonuclease, DNA binding activity, and RNA binding activity. APE1 catalyzes hydrolytic incision of phosphodiester bond and also has 3' exoribonuclease activity and 3' phosphodiesterase activity. APE1 also stimulates 5' dRp excision activity of Pol-β. An exemplary sequence for a human APE1 protein is provided at FIG. 15.

This figure contains SEQ ID NO: 1.

By "ameliorate" is meant decrease, suppress, attenuate, diminish, arrest, or stabilize the development or progression of a disease.

By "compound" is meant any small molecule chemical compound, antibody, nucleic acid molecule, or polypeptide, or fragments thereof.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "disease" is meant any condition or disorder that damages or interferes with the normal function of a cell, tissue, or organ.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "marker" is meant any protein or polynucleotide having an alteration in expression level or activity that is associated with a disease or disorder.

By "neoplasia" is meant a disease or disorder characterized by excess proliferation or reduced apoptosis. Illustrative neoplasms for which the invention can be used include, but are not limited to pancreatic cancer, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythernia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, eystadenocarcinoma, medullary carcinoma, bronchogenic carcinoma, renal cell carcinoma, hepatoma, vile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannorna, meningioma, melanoma, neuroblastoma, and retinoblastoma).

By "protein" or "polypeptide" or "peptide" is meant any chain of more than two natural or unnatural amino acids, regardless of post-translational modification (e.g., glycosylation or phosphorylation), constituting all or part of a naturally-occurring or non-naturally occurring polypeptide or peptide, as is described herein.

By "subject" is meant a mammal, including, but not limited to, a human or non-human mammal, such as a bovine, equine, canine, ovine, or feline.

By "reference" is meant a standard or control condition. In one embodiment, the effect of an agent on a cell is compared to the effect of the agent on a control cell.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and most preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, iso-leucine, leucine; aspartic acid, giutamic acid, asparagine, glutamine; serine, threonine; lysine, arginine; and phenyl-alanine, tyrosine. In an exemplary approach to determining the degree of identity, a BILVST program may be used, with a probability score between $e^{-3}$ and $e^{-100}$ indicating a closely related sequence.

"Therapeutic agent" means a substance that has the potential of affecting the function of an organism. Such a compound may be, for example, a naturally occurring, semi-synthetic, or synthetic agent. For example, an agent may be a drug that targets a specific function of an organism or an antibiotic. A therapeutic agent may decrease, suppress, attenuate, diminish, arrest, or stabilize the development or progression of disease, disorder, or infection in a eukaryotic host organism.

BRIEF DESCRIPTION OF THE DRAWINGS

FIG. 2A depicts NSC-30049. FIG. 2B depicts NSC-30049 derivatives.

FIG. 4A depicts an in vitro assay system to determine the effect of compounds on the blockage of APE1-activity using purified APE1 and $^{32}$P-labeled 63-mer F-DNA. FIG. 4B is a gel depicting the effect of the small molecules on APE1 activity. Lane 1 shows 63-mer $^{32}$P-labeled F-DNA, lane 2 shows 23-mer product after APE1 incision, lane 3 shows 1-nt incorporation (24-mer) and strand-displacement products, Lanes 3-6, 7-10, 11-14, 15-18 and 19-22 show the APE1 activity after incubation with 5, 10, 20 and 40 respectively of NSC-9746, NSC-18468, NSC-2137, NAC-30049 and NSC-32895. Data are representative of duplicate experiments.

FIG. 5A depicts an in vitro assay protocol using purified APE1 protein. FIG. 5B is an image of a gel showing a dose-dependent effect of NSC-30049 on APE1 activity. Lane 1 shows uncut 63-mer $^{32}$P-labeled F-DNA (3-hydroxy-2-hydroxymethyltetrahydrofuran (F) inserted at position 23 of DNA), Lane 2 shows 23-mer APE1 cleavage product, Lanes 3-7 show the effect of different concentrations of NSC-30049 (1, 2.5, 5, 7.5 and 10 nM, respectively) on APE1 activity. FIG. 5C is a graph depicting the percent cleavage and the $IC_{50}$ of NSC-30049 to block APE1 activity, showing that APE1 is blocked in a dose-dependent manner. Data is mean±SE of three different experiments.

FIG. 6A shows that NSC-30049 did not affect Pol-β-directed strand-displacement synthesis in vitro, Lane 1 represents $^{32}$P-labeled 63-mer F-DNA, Lane 2 shows 23-mer product after APE1 incision, and Lane 3 shows displacement activity in the presence of Poi-β. Lanes 4-7 contained increasing concentrations of NSC-30049 (0.5, 1, 2.5, and 5 µM, respectively). The arrows indicate the positions of the 63-mer substrate and the products. FIG. 6B shows that NSC-30049 did not affect Fen1 activity in vitro, Lane 1 shows the position of 51-mer labeled oligonucle-otide. $^{32}$P-labeled 63-mer F-DNA (2.5 nM) was incubated for 15 min with Fen1 (1 nM) without (lane 2) or with different concentrations of NSC-3049 (0.5, 1, 2, 5, and 5 µM; lanes 3-6 respectively). FIG. 6C shows that NSC-30049 did not affect DNA ligase I activity in vitro. Lane 1 shows 23-mer labeled oligonucleotide. $^{32}$P-labeled nicked DNA (2.5 nM) was incubated for 30 mM with 1 nM of DNA ligase I without (lane 2) or with different concentrations of NSC-30049 (0, 0.5, 1 µM; lanes 3-6, respectively). Data are representative of three different experiments.

FIG. 7A shows the 5'-fluorescein-labelled 32-mer duplex DNA (10 TIM) containing a tetrahydrofuran that was incubated with variable concentrations of APE1 (0, 0.30, 0.63, 0.94, and 1.25 µM) in 50 mM Hepes, pH 7.5 and 1 mM EDTA to determine fluorescence anisotropy. FIG. 7B is a table showing the apparent $K_d$ values of the data. Values are the mean±SD of triplicate estimations.

FIG. 8A depicts in situ imaging of orthotopic MiaPaCa2-Lu tumors growing in female athymic (nu/nu) mice. FIG. 8B is a graph depicting a synergistic effect on the growth inhibition of tumors after combination treatment of NSC-30049 and CDDP. *, Significantly different than control ($p<0.05$).

FIG. 9A shows that NSC-30049 and OPT inhibit the growth of human parental cancer cells and colon cancer stem cells. Cells were treated with 1.25 µM of NSC-30049 and 1.25 µM of OPT either alone or in combination for 72 h. Data are mean±SD of triplicate experiments. FIG. 9B depicts the inhibition in expression of self-renewal marker genes of colon cancer stem cells, qRT-PCR data of CD133+, Oct4, Sox2 and Nanog gene expression levels of parental cancer cells and colon cancer stem cells was obtained. Cells were treated with 1.25 µM of NSC-30049 and 1.25 µM of OPT either alone or in combination for 72 h. Fold change in gene expression values is shown as mean±SD of three experiments and are normalized to GAPDH gene expression.

FIG. 10A is a schematic representation of the experimental protocol. FIG. 10B shows the change in tumor volume from the day of transplant to the 38$^{th}$ day of the experiment. Data are the mean±SD of four to six animals in each group.

FIG. 11A is a graph depicting the viability of U87MG cancer cell line in cultures incubated with various concentrations of TMZ and NSC-30049. FIG. 11B is a graph depicting the viability of GBM-LO cancer cell line in cultures incubated with various concentrations of TMZ and NSC-30049. For spheroid viability, spheroid formation assay was initiated using GBM-U87MG and GBM-L0 cancer-initiating cells. Single cell suspension was prepared from brain spheroid GBM-U87MG and GBM-L0 cells by trypsinization and re-suspending in PBS (containing 0.01% EDTA) followed by incubation at 37° C. for 10 min. For spheroid assay, 1,000 single cells in suspensions were plated in triplicate in each well of 12-well plates. Cells were pre-treated with 2.5 µM of NSC-30049 or 10 or 100 µM of TMZ alone or in combination with NSC-30049 for 168 h. Then, spheroids were trypsinzed again and resuspended in a medium containing growth factor. Viability of cancer-initiating cells was determined by trypan blue exclusion assay. Data presented are the mean±SE of three different estimations.

FIG. 12A is a graph depicting the number of U87MG spheroids when cultures were incubated with various concentrations of TMZ and NSC-30049. Data presented are the mean±SE of three different estimations. FIG. 12B are representative images of U87MG spheroids incubated with various concentrations of TMZ and NSC-30049. Spheroid formation was initiated using GBM-U87 cancer-initiating cells. Single cell suspension was prepared from brain spheroid GBM-U87MG cells by trypsinization. For the spheroid assay, 1,000 single cells were plated in triplicate in a 12-well plate. Cells were pretreated with 2.5 µM of NSC30049 or 10 or 100 µM of TMZ alone or in combination with NSC-30049 for 168 h. Then, spheroids containing 4 or more cells were counted.

FIG. 13A is a graph depicting the number of GBM-LO spheroids when cultures were incubated with various concentrations of TMZ and NSC-30049. Data presented are the mean±SE of three different estimations. FIG. 13B are representative images of GBM-LO spheroids incubated with various concentrations of TMZ and NSC-30049. Spheroids formation was initiated using GBM-LO cancer-initiating cells. Single cell suspension was prepared from brain spheroid GBM-LO cells by trypsinization. For spheroid assay, 1,000 single cells were plated in triplicate in a 12-well plate. Cells were pretreated with 2.5 µM of NSC-30049 or 10 or 100 µM of TMZ alone or in combination with NSC-30049 for 168 h. Then, spheroids containing 4 or more cells were counted.

FIG. 14A shows that combination treatment of NSC-30049 with TMZ reduced the expression of self-renewal genes of cancer initiating glioblastoma cell line, GBM-LO stem in vitro. Cells were pretreated with 2.5 µM of NSC30049 or 10 or 100 µM TMZ alone or in combination with NSC-30049 for 36 h. Then, total RNA was isolated and processed for qRT-PCR. Data presented are the mean±SE of three different measurements. FIG. 14B shows that combination treatment of NSC-30049 with TMZ reduced the expression of aldehyde dehydrogenase gene Aldh1a1 in cancer initiating glioblastoma cell line, GBM-LO stem in vitro. Treatment with NSC-30049 or TMZ reduced the expression of aldehyde dehydrogenase gene Aldh1a7 in GBM-LO stem cell line in vitro, but not treatment with NSC-30049 and TMZ. Cells were pretreated with 2.5 µM of NSC-30049 or 10 or 100 µM of TMZ alone or in combination with NSC-30049 for 36 h. Then, total RNA was isolated and processed for qRT-PCR. Data presented are the mean±SE of three different measurements.

FIG. 15 provides the amino acid sequence for a human Apurinic/apyrimidinic (AP) endonuclease (APE1), which corresponds to NCBI Accession No. P27695.

Figure 1:
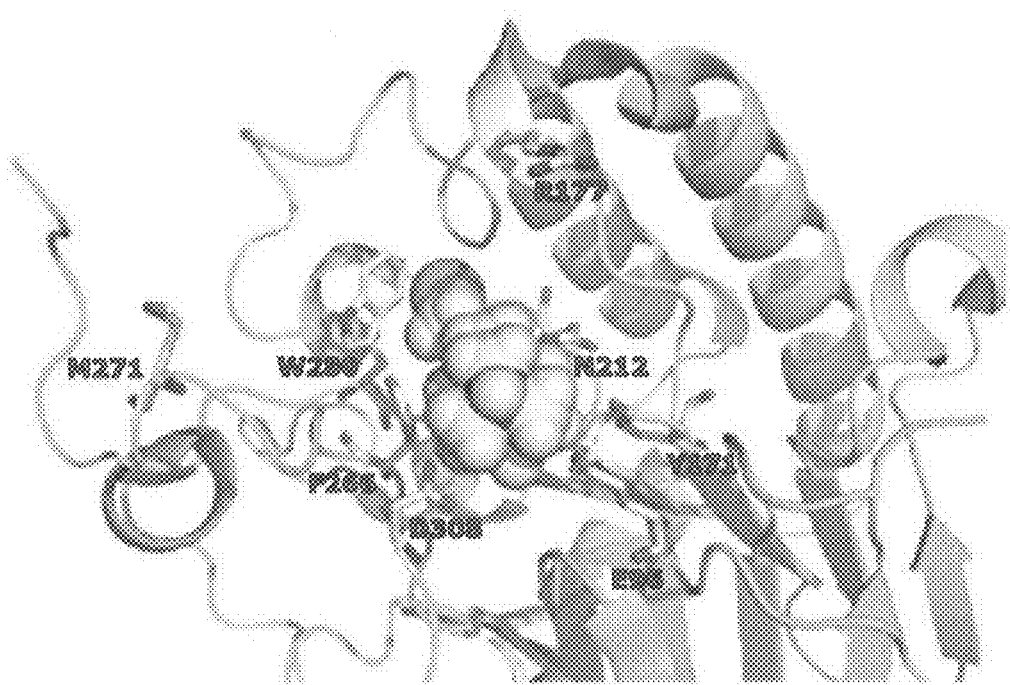
FIG. 1 is a space-filling model depicting the molecular docking of NSC-30049 at the catalytic domain of APE1. NSC-30049 exhibits a high molecular docking score of –50.9657 0 kcal/mol. The molecular surface of the catalytic domain of APE1 is formed by the amino acid residues E96, Y171, D210, N212, F266, W280, L282, and D308 and displayed an interaction with SMI NSC-30049.

This figure contains SEQ ID NO: 1.

DETAILED DESCRIPTION OF THE INVENTION

The invention features compositions and methods that are useful for enhancing the efficacy of DNA-alkylating drugs for the treatment of neoplasia (e.g., pancreatic cancer, colon cancer, and brain cancers, such as glioblastoma). In particular, the invention provides compositions comprising cisplatin (CDDP) and/or gemcitabine (dFdC) in combination with NSC-30049; and methods of using the composition for the treatment of pancreatic cancer. In other embodiments, the invention provides compositions comprising NSC-30049 administered in combination with temozolomide or oxaliplatin.

The invention is based, at least in part, on several surprising discoveries: that NSC-30049 and gemcitabine when administered in combination with cisplatin results in a increased sensitivity to cisplatin; and that NSC-30049 and gemcitabine synergistically enhance the effectiveness of cisplatin by blocking base excision repair (BER) and nucleotide excision repair in pancreatic cancer. These discoveries are applicable to other neoplasias. When NSC-30049 was administered in combination with temozolomide or oxaliplatin, the combination reduced growth of colon cancer cells. NSC-30049 in combination with temozolomide was also effective in reducing the growth of glioblastoma cells. In view of these discoveries, other agents that bind APE1 within the active site are expected to be equally effective for the treatment of a variety of neoplasias, including pancreatic cancer, colon cancer, and brain cancers (e.g., glioblastoma).

Pancreatic Cancer

Increased knowledge of the tumorigenesis cascade in pancreatic cancer has led to directed therapeutic approaches that are tailored to specific tumor type. In addition to this heterogeneity, the microarray gene profiling data that has been generated in the past several years suggest an even greater heterogeneity of tumor type. As the available treatment modalities depend largely on the status of the tumor, such an approach requires the development of an alternative chemotherapeutic/chemopreventive strategy. The present invention provides a treatment strategy that can be used to manage all of these types of tumors, and therefore represents a major advance in patient care. The present invention is founded on the recognition that combinatorial therapeutic strategies can provide dramatic improvements over monotherapeutic regimens.

In particular embodiments, the invention provides compositions and methods for the treatment of neoplasia featuring cisplatin in combination with any one or more of gemcitabine and NSC-30049. A combination of chemopreventive and chemotherapeutic agents to block DNA repair and multiple oncogenic pathways is more efficacious than the use of single agents for the management of cancer, e.g., pancreatic cancer, colon cancer, and brain cancer, such as glioblastoma.

In other embodiments, the invention features compositions and methods that are useful for the treatment of a neoplasia (e.g., pancreatic cancer, colon cancer, and brain cancer, such as glioblastoma) by potentiating the efficacy of DNA alkylating agents using small molecules that interfere with the Base Excision Repair (BER) and Nucleotide Excision Repair (NER) DNA repair pathways. The chemotherapeutic drugs, which induce DNA-alkylation damage, are primarily repaired by the BER and NER pathways. Anticancer drugs as inhibitors of these DNA-repair systems have emerged, but the targets have been mainly the $O^6$-methylguanine DNA-methyltransferase (MGMT)/mismatch repair (MMR) pathways. The blockade of the BER pathway has been largely overlooked, although in the case of DNA-alkylating drug, Temozolomide (TMZ), BER is responsible for the repair of 70% and 9% of $N^7$-Methyl guanine and $N^3$-methyl adenine lesions, respectively. Structure-based screening of small molecular weight inhibitors identified small molecule inhibitors (SMIs), including NSC-30049 that interacts within the active site of APE1 and blocks the APE1-directed BER pathway. Accordingly, use of these inhibitors in combination with cisplatin, oxiplatin, temozolomide, and/or other alkylating agents, synergistically increases therapeutic efficacy, reduces adverse side effects, thereby providing an advance over existing monotherapies.
The Base Excision Repair (BER) Pathway Exogenous and endogenous mutagenic agents attack the genomes of all living cells. DNA bases damaged by these agents may be cytotoxic and/or miscoding, and are thought to be a major source of intermediates in tumorigenesis. DNA repair systems efficiently remove damaged DNA via several different pathways that reverse the vast majority of genetic lesions formed during the life span of a cell. Most DNA repair mechanisms, including the base excision repair pathway, involve the participation of enzymes and other proteins that recognize structural alterations in DNA. Estimates of the number of abasic sites generated by mammalian cells are approximately $10^6$/cell/day. Abasic sites are unstable and degrade spontaneously into DNA-strand breaks by β-elimination that retards DNA polymerases. They are highly mutagenic because of non-template DNA and RNA synthesis. Despite the large number of abasic sites generated per cell per day, the number of resulting mutations is extremely low. This disparity underscores the importance of the elaborate mechanisms that the cell has devised to repair abasic sites. Deficiencies in the DNA repair pathways usually have catastrophic consequences for the affected organisms. In humans, deficiency in DNA repair has been linked to a number of genetic diseases characterized by radiation sensitivity and cancer-prone syndromes.

In mammalian cells, base excision repair can proceed through at least two pathways distinguished by the repair patch size as well as by the contribution of different proteins involved in the pathway. These are designated as "single nucleotide (SN)-base excision repair" and "multinucleotide or long-patch (LP)-base excision repair" pathways. In both pathways, repair is initiated by the initial recognition and removal of the modified base by a DNA glycosylase generating an abasic site (AP-site). There are two types of DNA glycosylases—monofunctional and bifunctional. Monofunctional DNA glycosylases cleave only the glycosidic bond between N and Cl' and then protect the abasic site until apurinic/apyrimidinic (AP) endonuclease 1 (APE-1) cleaves the DNA backbone at the 5'-end of the AP-site. The bifunctional DNA glycosylases have additional AP-lyase activity. The DNA glycosylase cleaves a glycosidic bond between the sugar and the base to establish an abasic-site. Subsequently, APE-1 cleaves the DNA backbone generating a 3'-OH and 5'-deoxyribose phosphate (5'-dRP) ends. Subsequently, the remaining 5'-dRP residue is cleaved by a 5'-deoxyribose phosphate lyase (dRP-lyase) activity of pol-1 to yield a 5'-phosphorylated gapped-DNA strand. Pol-β then incorporates the correct base at the site of the damaged base with its polymerizing activity and DNA ligase-I or III seals the nick. This repair process becomes complicated once the AP-site is oxidized or reduced. In this case, the dRP-lyase activity of pol-β is interrupted and the repair of DNA is accomplished through long patch-base excision repair. Under these circumstances, the pol-β-dependent strand-displacement synthesis generates longer repair patch and a 5'-overhang of a single-stranded DNA-flap with a modified sugar at its 5'-end. The 5'-overhang DNA-flap is cleaved by flap endonuclease 1 (Fen-1), and finally the nick is sealed by DNA ligase I or III.

The APE1 mediated base excision repair (BER) pathway or the nucleotide excision repair NER pathways play a key role in the responses of cells to alklyating agents that damage DNA. Indeed, the extent and type of DNA damage incurred on exposure to the alkylating agents plays a role in determining the type of BER response. It also determines whether the cell continues to attempt to repair the damage, or in the face of extensive damage, switches to an apoptotic response to eliminate the cell. The latter phenomenon is exploited in the use of alkylating agents as chemotherapeutic agents. It is well established that APE1 plays a key role at least in colorectal carcinogenesis, and interacts with DNA in the base excision repair (BER) pathway.

As reported in more detail below, the treatment of human pancreatic cancer cells with the DNA alkylating agent cisplatin (CDDP) increases DNA damage, which requires the activity of the BER and NER pathways for DNA repair. Blocking either the BER and NER pathways results in increased sensitivity and cell death of cells harboring damaged DNA. In addition, exposure of human pancreatic cancer cells to APE1 inhibitor, e.g., NSC-30049, enhances the cytotoxicity of cisplatin. Furthermore exposure of human pancreatic cancer cells to a combination of a APE1 inhibitor, e.g., NSC-30049, and gemcitabine further enhances the cytotoxicity of cisplatin. These observations were also applicable to colon and brain cancer.
Apurinic/Apyrimidinic (AP) Endonuclease (APE1)

Apurinic/apyrimidinic (AP) endonuclease (APE1) is a multifunctional protein that plays roles role in the DNA base excision repair (BER) pathway and the cellular response to oxidative stress. The C-terminus exerts DNA AP-endodeoxyribonuclease activity, while the N-terminus of APE1 contains the redox activity. Both functions are independent in their actions.

The amino acid sequence of APE1 is provided at NCBI Reference No. NCBI Accession No. P27695, which is reproduced below:

```
  1 mpkrgkkgav aedgdelrte peakksktaa kkndkeaage gpalyedppd qktspsgkpa 61 tlkicswnvd glrawikkkg ldwvkeeapd ilclqetkcs enklpaelqe lpglshqyws 121 apsdkegysg vgllsrqcpl kvsygigdee hdqegrviva efdsfvlvta yvpnagrglv 181 rleyrqrwde afrkflkgla srkplvlcgd lnvaheeidi rnpkgnkkna gftpqerqgf 241 gellqavpla dsfrnlypnt pyaytfwtym mnarsknvgw rldyfllshs llpalcdski 301 rskalgsdhc pitlylal
```

(SEQ ID NO: 1)
APE1 is a 318-amino acid polypeptide. APE1 catalyzes hydrolytic incision of phosphodiester bond and also has 3' exoribonuclease activity and 3' phosphodiesterase activity. APE1 also stimulates 5'dRp excision activity of Pol-β. APE1 binds to both DNA and RNA.

In the BER pathway, APE1 functions as a apurinic/apyrimidinic (AP) endodeoxyribonuclease in the repair of DNA lesions induced by oxidative and alkylating agents. APE1 initiates repair of AP sites in DNA by catalyzing hydrolytic incision of the phosphodiester backbone immediately adjacent to the damage, generating a single-strand break with 5'-deoxyribose phosphate and 3'-hydroxyl ends. The C—O—P bond 3' to the apurinic or apyrimidinic site in DNA is broken by APE1 in a beta-elimination reaction, leaving a 3'-terminal unsaturated sugar and a product with a terminal 5'-phosphate. APE1 possesses a DNA 3' phosphodiesterase activity capable of removing lesions (such as phosphoglycolate) blocking the 3' side of DNA strand breaks. Acts as a loading factor for POLB onto non-incised AP sites in DNA and stimulates the 5'-terminal deoxyribose 5'-phosphate (dRp) excision activity of Pol-β. These properties of APE1 suggest a role for APE1 as a target in base excision repair and chemoprevention.

Pol-β

Pol-β is the smallest eukaryotic DNA polymerase. It is a 39-kDa protein and consists of an 8-kDa amino-terminal domain with dRP-lyase and 5'-phosphate recognition activities, and a 31-kDa carboxyl-terminal domain with nucleotidyltransferase activity (Beard et al., (2006) Chem. Rev. 106, 361-382). The 8- and 31-kDa domains of pol-β are connected by a protease-hypersensitive region, known as the linker-region (Kumar et al., (1990) Biochemistry 29, 7156-7159; Beard, W. A., and Wilson, S. H. (1995) Methods Enzymol. 262, 98-107). Pol-β has the ability to fill short DNA gaps, but lacks an associated exonuclease or proofreading activity (Singhal, R. K., and Wilson, S. H. (1993) J. Biol. Chem. 268, 15906-15911). The 31-kDa carboxyl-terminal polymerase domain is composed of three functionally distinguishable subdomains. First, the catalytic C-subdomain, which coordinates two divalent metal cations, assists the nucleotidyl transferase reaction in base excision repair. Second, the D-subdomain which has a primary role in duplex DNA-binding; and the N-subdomain provides interactions with the nascent base pair (nucleoside 5'-triphosphate and templating nucleotide) (Beard et al., (2006) Chem. Rev. 106, 361-382). These subdomains correspond to the palm, thumb, and fingers subdomains, respectively, for right-handed DNA polymerases (Beard et al., (2006) Chem. Rev. 106, 361-382, 35).

The crystal and solution structures of the amino-terminal 8-kDa lyase domain (amino acids 1-87) have been determined (Pelletier et al., (1994) Science 264, 1891-1903, Liu et al., (1996) Biochemistry 35, 6188-6200). This domain is composed of two pairs of antiparallel α-helices and possesses the dRP-lyase activity. The lyase domain also contains a motif termed "Helix-hairpin-Helix (HhH)", which is common in many other DNA repair proteins (Pelletier, H., and Sawaya, M. R. (1996) Biochemistry 35, 12778-12787). Biochemical and crystallography studies indicate that Lys72 plays a role in the lyase reaction mechanism. This reaction proceeds via a Schiff-base intermediate between pol-β and the 5'-dRP residue of the substrate, whereby the side chain of Lys72 provides the nucleophile for the completion of the reaction. The involvement of the lyase domain in strand-displacement synthesis of pol-β remains to be identified.

Base Excision Repair as a Chemotherapeutic Target

Defects in the base excision repair pathway can cause cytotoxic accumulation of lesions in cell genomic DNA. This accumulation of lesions has been exploited as a chemotherapeutic target for killing cancer cells. DNA-alkylating agents are commonly used to induce genetic lesions in cancer cells for the treatment of brain tumors, ovarian cancer, malignant melanomas, and various hematological tumors. These DNA-alkylating agents have either one or two reactive groups that interact covalently with nucleophilic centers in DNA. Such reactive sites are present in all four bases, and they are attacked with different affinities and specificities. Most reactive sites are the ring nitrogen atoms—in particular $N^7$ of guanine ($N^7mG$) and $N^3$ of adenine ($N^3mA$), but alkylation also occurs at less nucleophilic oxygens, such as the $O^6$ position of guanine ($O^6mG$). The $N^7mG$ and $N^3$ mA are very common lesions and under normal circumstances they are repaired by base excision repair. Although a number of APE1 inhibitors have been reported, more potent and selective inhibitors of APE1 are still needed. One approach to the identification of such agents is to sensitize cancer cells to DNA-damaging agents by inhibiting various proteins in the DNA repair pathways. Small chemical compounds have been identified by molecular docking or NMR studies to target the base excision repair pathway by inhibiting apurinic/apyrimidinic endonuclease and pol-if activities. There is a need for agents that can block APE1 base excision repair. Thus, agents that target the endonuclease site of APE1 may be used to target APE1-mediated sensitization of cancer cells.

Compounds of the Invention

Compounds, such as NSC-30049, and other compounds that bind to amino acid residues of APE1 that function in the endonuclease catalytic site of APE1 (e.g., E96, Y171, D210, N212, F266, W280, L282, and D308) are useful for the treatment of neoplasias, such as pancreatic cancer, glioblastomas, lung cancer, and colon cancer, alone or in combination with an alkylating agent, such as cisplatin. Without wishing to be bound by theory, these compounds may be particularly effective against neoplastic cells because they are capable of interacting with and reducing the activity of APE1. In one approach, compounds useful for the treatment of neoplasia are selected using a molecular docking program to identify compounds that bind to APE1 at an APE1 endonuclease site (e.g., a APE1 site comprising at least amino acid residues E96, Y171, D210, N212, F266, W280, L282, and D308). In certain embodiments, a compound of the invention binds to APE1 and reduces BER activity, APE1 endonuclease activity, or APE1 DNA binding activity.

In certain embodiments, a compound of the invention can prevent, inhibit, or disrupt, or reduce by at least 10%, 25%, 50%, 75%, or 100% the activity of a BER pathway by binding to an APE1 endonuclease site in APE1.

In certain embodiments, a compound of the invention is a small molecule having a molecular weight less than about 1000 daltons, less than 800, less than 600, less than 500, less than 400, or less than about 300 daltons. Examples of compounds of the invention include NSC-30049, and pharmaceutically acceptable salts thereof.

The term "pharmaceutically acceptable salt" also refers to a salt prepared from a compound of the invention having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)-amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)-amine, or tri-(2-hydroxyethyl)amine; N-methyl-D-glucamine; and amino acids such as arginine, lysine, and the like. The term "pharmaceutically acceptable salt" also refers to a salt prepared from a compound disclosed herein, e.g., NSC-30049, having a basic functional group, such as an amino functional group, and a pharmaceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

An anti-neoplasia therapeutic, such as NSC-30049, may be administered in combination with any other standard anti-neoplasia therapy or conventional chemotherapeutic agent, such as an alkylating agent; such methods are known to the skilled artisan and described in Remington's Pharmaceutical Sciences by E. W. Martin. If desired, agents of the invention are administered in combination with any conventional anti-neoplastic therapy, including but not limited to, surgery, radiation therapy, or chemotherapy. Conventional chemotherapeutic agents include, but are not limited to, alemtuzumab, altretamine, aminoglutethimide, amsacrine, anastrozole, azacitidine, bleomycin, bicalutamide, busulfan, capecitabine, carboplatin, carmustine, celecoxib, chlorambucil, 2-chlorodeoxyadenosine, cisplatin, colchicine, cyclophosphamide, cytarabine, cytoxan, dacarbazine, dactinomycin, daunorubicin, docetaxel, doxorubicin, epirubicin, estramustine phosphate, etodolac, etoposide, exemestane, floxuridine, fludarabine, 5-fluorouracil, flutamide, formestane, gemcitabine, gentuzumab, goserelin, hexamethylmelamine, hydroxyurea, hypericin, ifosfamide, imatinib, interferon, irinotecan, letrozole, leuporelin, lomustine, mechlorethamine, melphalen, mercaptopurine, 6-mercaptopurine, methotrexate, mitomycin, mitotane, mitoxantrone, nilutamide, nocodazole, paclitaxel, pentostatin, procarbazine, raltitrexed, rituximab, rofecoxib, streptozocin, tamoxifen, temozolomide, teniposide, 6-thioguanine, topotecan, toremofine, trastuzumab, vinblastine, vincristine, vindesine, and vinorelbine. In one preferred embodiment, an agent that binds to an APE1 endonuclease site on APE1 (e.g., NSC-30049) and reduces APE1 activity is administered in combination with cisplatin. In another preferred embodiment, an agent that binds to an APE1 endonuclease site on APE1 (e.g., NSC-30049) and reduces APE1 activity and an agent that binds to ribonucleotide reductase (RR) and reduces nucleotide synthesis relative to a reference is gemcitabine or a chemopreventive agent are administered in combination with cisplatin.

In Silico Screening Methods and Systems

Methods for designing, evaluating and identifying compounds that bind to the aforementioned binding site are apparent to one of skill in the art using a machine readable storage medium which comprises the structural coordinates of an APE1 endonuclease site in APE1 identified herein (e.g., amino acids 60-120, 60-170, 80-170, or another fragment containing E96, Y171, D210, N212, F266, W280, L282, and D308). A storage medium encoded with these data is capable of displaying a three-dimensional graphical representation of a molecule or molecular complex which comprises such binding sites on a computer screen or similar viewing device. Compounds identified in such a way are expected to be cytotoxic, to inhibit APE biological activity (e.g., APE1 endonuclease activity; APE1 DNA binding activity) and/or to reduce the activity of a BER pathway. A computer may be used for producing a) a three-dimensional representation of a molecule or molecular complex, wherein said molecule or molecular complex comprises a binding site; or b) a three-dimensional representation of a homologue of said molecule or molecular complex, wherein said homologue comprises a binding site that has a root mean square deviation from the backbone atoms of said amino acids of not more than about 2.0 (more preferably not more than 1.5) angstroms. Such a computer may comprise:

(i) a machine-readable data storage medium comprising a data storage material encoded with machine-readable data, wherein said data comprises the structure coordinates of amino acid residues in the APE1 endonuclease site;

(ii) a working memory for storing instructions for processing said machine-readable data;

(iii) a central-processing unit coupled to said working memory and to said machine-readable data storage medium for processing said machine readable data into said three-dimensional representation; and (iv) a display coupled to said central-processing unit for displaying said three-dimensional representation.

Thus, the computer produces a three-dimensional graphical structure of a molecule or a molecular complex which comprises a binding site.

The computer may also comprise a machine-readable data storage medium for producing a three-dimensional representation of a molecule or molecular complex defined by structure coordinates of all of the APE1 amino acids, or a three-dimensional representation of a homologue of said molecule or molecular complex, wherein said homologue comprises a binding site that has a root mean square deviation from the backbone atoms of said amino acids of not more than 2.0 (more preferably not more than 1.5) angstroms.

In exemplary embodiments, the computer or computer system can include components that are conventional in the art, e.g., as disclosed in U.S. Pat. Nos. 5,978,740 and/or 6,183,121 (incorporated herein by reference). For example, a computer system can include a computer comprising a central processing unit ("CPU"), a working memory (which may be, e.g., RAM (random-access memory) or "core" memory), a mass storage memory (such as one or more disk drives or CD-ROM drives), one or more cathode-ray tube (CRT) or liquid crystal display (LCD) display terminals, one or more keyboards, one or more input lines, and one or more output lines, all of which are interconnected by a conventional system bus.

Machine-readable data of this invention may be inputted to the computer via the use of a modem or modems connected by a data line. Alternatively or additionally, the input hardware may include CD-ROM drives, disk drives or flash memory. In conjunction with a display terminal, a keyboard may also be used as an input device.

Output hardware coupled to the computer by output lines may similarly be implemented by conventional devices. By way of example, output hardware may include a CRT or LCD display terminal for displaying a graphical representation of a binding pocket of this invention using a program such as QUANTA or PYMOL. Output hardware might also include a printer, or a disk drive to store system output for later use.

In operation, the CPU coordinates the use of the various input and output devices, coordinates data accesses from the mass storage and accesses to and from working memory, and determines the sequence of data processing steps. A number of programs may be used to process the machine-readable data of this invention, including commercially-available software.

A magnetic storage medium for storing machine-readable data according to the invention can be conventional. A magnetic data storage medium can be encoded with a machine-readable data that can be carried out by a system such as the computer system described above. The medium can be a conventional floppy diskette or hard disk, having a suitable substrate which may be conventional, and a suitable coating, which may also be conventional, on one or both sides, containing magnetic domains whose polarity or orientation can be altered magnetically. The medium may also have an opening (not shown) for receiving the spindle of a disk drive or other data storage device.

The magnetic domains of the medium are polarized or oriented so as to encode in a manner which may be conventional, machine readable data such as that described herein, for execution by a system such as the computer system described herein.

An optically-readable data storage medium also can be encoded with machine-readable data, or a set of instructions, which can be carried out by a computer system. The medium can be a conventional compact disk read only memory (CD-ROM) or a rewritable medium such as a magneto-optical disk which is optically readable and magneto-optically writable.

In the case of CD-ROM, as is well known, a disk coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, a data-recording coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Structure data, when used in conjunction with a computer programmed with software to translate those coordinates into the 3-dimensional structure of a molecule or molecular complex comprising an APE1 endonuclease site may be used for a variety of purposes, such as drug discovery.

For example, the structure encoded by the data may be computationally evaluated for its ability to associate with chemical entities. Chemical entities that associate with a binding site or catalytic site of an APE1 protein are expected to be toxic to neoplastic cells (e.g., glioblastoma, lung cancer, colon cancer cells), to inhibit base excision repair, or to enhance the efficacy of an alkylating agent. Such compounds are potential drug candidates. Alternatively, the structure encoded by the data may be displayed in a graphical three-dimensional representation on a computer screen. This allows visual inspection of the structure, as well as visual inspection of the structure's association with chemical entities.

Thus, using computational methods it is possible to evaluate the potential of a chemical entity to associate with a) a molecule or molecular complex comprising a binding site defined by structure coordinates of APE1, as described herein, or b) a homologue of said molecule or molecular complex, wherein said homologue comprises a binding pocket that has a root mean square deviation from the backbone atoms of said amino acids of not more than 2.0 (more preferably 1.5) angstroms.

Such a method may comprises the steps of:

i) employing computational means to perform a fitting operation between the chemical entity and a binding site of the APE1 polypeptide or fragment thereof or molecular complex; and ii) analyzing the results of the fitting operation to quantify the association between the chemical entity and the APE1 endonuclease site. This embodiment relates to evaluating the potential of a chemical entity to associate with or bind to a binding site of an APE1 polypeptide or fragment thereof.

The term "chemical entity", as used herein, refers to chemical compounds, complexes of at least two chemical compounds, and fragments of such compounds or complexes.

Such a method may also be used to evaluate the potential of a chemical entity to associate with a molecule or molecular complex defined by structure coordinates of all of the amino acids of APE1 protein, as described herein, or a homologue of said molecule or molecular complex having a root mean square deviation from the backbone atoms of said amino acids of not more than 2.0 (more preferably not more than 1.5) angstroms.

Additionally, using computational methods the structural coordinates of one of the binding sites described herein can be utilized in a method for identifying an antagonist of a molecule comprising a APE1 endonuclease site (e.g., an endonuclease catalytic site or binding site within the APE1 sequence). This method comprises the steps of:

a) using the atomic coordinates of APE1;

b) employing the three-dimensional structure to design or select the potential agonist or antagonist. The method further includes the optional steps of c) synthesizing the agonist or antagonist; and d) contacting the agonist or antagonist with the molecule to determine the ability of the potential agonist or antagonist to interact with the molecule. If desired, the method further involves the step of contacting a neoplastic cell (e.g., glioblastoma cell) with a APE1 binding compound and evaluating cytotoxicity in the presence or the absence of an alkylating agent, evaluating neoplastic cell proliferation, cell death, or BER activity.

Additionally, using computational methods it is possible to identify a potential antagonist of APE1 polypeptide, comprising the steps of:

a) using the atomic coordinates of the APE1 polypeptide (e.g., APE1 endonuclease site sequence, including at least about E96, Y171, D210, N212, F266, W280, L282, and D308 amino acid residues of APE1, or other residues that are involved in the endonuclease activity of APE1); and b) employing the three-dimensional structure to design or select the potential antagonist.

Knowledge of the APE1 endonuclease site of a APE1 polypeptide provides the necessary information for designing new chemical entities and compounds that may interact with APE1 proteins, in whole or in part, and may therefore modulate (e.g., inhibit) the activity of APE1 proteins.

The design of compounds that bind to a APE1 sequence, that are cytotoxic to a neoplastic cell, or that reduce APE1 expression or biological activity, according to this invention generally involves consideration of several factors. In one embodiment, the compound physically and/or structurally associates with at least a fragment of a APE1 polypeptide, such as an APE1 endonuclease site within a APE1 sequence. Non-covalent molecular interactions important in this association include hydrogen bonding, van der Waals interactions, hydrophobic interactions and electrostatic interactions. Desirably, the compound assumes a conformation that allows it to associate with the APE1 endonuclease site(s) directly. Although certain portions of the compound may not directly participate in these associations, those portions of the entity may still influence the overall conformation of the molecule. This, in turn, may have a significant impact on the compound's potency. Such conformational requirements include the overall three-dimensional structure and orientation of the chemical compound in relation to all or a portion of the binding site, or the spacing between functional groups comprising several chemical compound that directly interact with the binding site or a homologue thereof.

The potential inhibitory or binding effect of a chemical compound on a APE1 endonuclease site may be analyzed prior to its actual synthesis and testing by the use of computer modeling techniques. If the theoretical structure of the given compound suggests insufficient interaction and association between it and the target binding site, testing of the compound is obviated. However, if computer modeling indicates a strong interaction, the molecule is synthesized and tested for its ability to bind a APE1 sequence or to test its biological activity by assaying for example, cytotoxicity in a neoplastic cell, by assaying an increase in the efficacy of an alkylating agent in a neoplastic cell. Candidate compounds may be computationally evaluated by means of a series of steps in which chemical entities or fragments are screened and selected for their ability to associate with the APE1 endonuclease site.

One skilled in the art may use one of several methods to screen chemical compounds, or fragments for their ability to associate with a APE1 endonuclease site. This process may begin by visual inspection of, for example, a APE1 endonuclease site on the computer screen based on the a APE1 structure coordinates described herein, or other coordinates which define a similar shape generated from the machine-readable storage medium. Selected fragments or chemical compounds are then positioned in a variety of orientations, or docked, within that binding site as defined supra. Docking may be accomplished using software such as Quanta and DOCK, followed by energy minimization and molecular dynamics with standard molecular mechanics force fields, such as CHARMM and AMBER.

Specialized computer programs (e.g., as known in the art and/or commercially available and/or as described herein) may also assist in the process of selecting fragments or chemical entities.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of the target binding site.

Instead of proceeding to build an inhibitor of a binding pocket in a step-wise fashion one fragment or chemical entity at a time as described above, inhibitory or other binding compounds may be designed as a whole or "de novo" using either an empty binding site or optionally including some portion(s) of a known inhibitor(s). There are many de novo ligand design methods known in the art, some of which are commercially available (e.g., LeapFrog, available from Tripos Associates, St. Louis, Mo.).

Other molecular modeling techniques may also be employed in accordance with this invention (see, e.g., N. C. Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once a compound has been designed or selected, the efficiency with which that entity may bind to a binding site may be tested and optimized by computational evaluation.

Specific computer software is available in the art to evaluate compound deformation energy and electrostatic interactions. Examples of programs designed for such uses include: AMBER; QUANTA/CHARMM (Accelrys, Inc., Madison, Wis.) and the like. These programs may be implemented, for instance, using a commercially-available graphics workstation. Other hardware systems and software packages will be known to those skilled in the art.

Another technique for identifying APE1 inhibitors involves the in silico screening of virtual libraries of compounds, e.g., as described herein (see, e.g., Examples). Many thousands of compounds can be rapidly screened and the best virtual compounds can be selected for further screening (e.g., by synthesis and in vitro or in vivo testing). Small molecule databases can be screened for chemical entities or compounds that can bind, in whole or in part, to an APE endonuclease site. In this screening, the quality of fit of such entities to the binding site may be judged either by shape complementarity or by estimated interaction energy.

Using computational methods to identify APE1 inhibitors, one of skill in the art may produce a three-dimensional representation of a) a molecule or molecular complex, wherein said molecule or molecular complex comprises a binding site in the linker sequence of a APE1 polypeptide defined by structure coordinates of amino acid residues in the APE1 endonuclease site; or b) a three-dimensional representation of a homologue of said molecule or molecular complex, wherein said homologue comprises a binding site that has a root mean square deviation from the backbone atoms of said amino acids of not more than about 2.0 (more preferably not more than 1.5) angstroms. Such a computer may comprise:

(i) a machine-readable data storage medium comprising a data storage material encoded with machine-readable data, wherein said data comprises the structure coordinates of structure coordinates of amino acid residues in the APE1 endonuclease site of a APE1 polypeptide;

(ii) a working memory for storing instructions for processing said machine-readable data;

(iii) a central-processing unit coupled to said working memory and to said machine-readable data storage medium for processing said machine readable data into said three-dimensional representation; and (iv) a display coupled to said central-processing unit for displaying said three-dimensional representation. As described in the Examples, compounds identified using in silico methods may optionally be tested in vitro or in vivo, for example, using the "Additional Screening Methods" described below, or any other method known in the art.

Additional Screening Methods

As described above, the invention provides specific examples of chemical compounds that are cytotoxic to neoplastic cells when administered alone or in combination with an alkylating agent. However, the invention is not so limited. The invention further provides a simple means for identifying agents (including nucleic acids, peptides, small molecule inhibitors, and mimetics) that are capable of binding to a APE1 polypeptide, for example, binding to an APE1 endonuclease site, and that are cytotoxic to a neoplastic cell, particularly when administered in combination with an alkylating agent or other chemotherapeutic. Such compounds are also expected to be useful for the treatment or prevention of a neoplasia (e.g., pancreatic cancer, colon cancer, glioblastoma, lung cancer).

In particular, because agents that bind to APE1 at an APE1 endonuclease site reduce the activity of a BER pathway, such agents are likely useful as therapeutics for the treatment or prevention of a neoplasia.

Virtually any agent that specifically binds to a APE1 polypeptide and that reduces BER activity may be employed in the methods of the invention. Methods of the invention are useful for the high-throughput low-cost screening of candidate agents that reduce, slow, or stabilize the growth or proliferation of a neoplasia. A candidate agent that specifically binds to APE1 is then isolated and tested for activity in an in vitro assay or in vivo assay for its ability to reduce neoplastic cell proliferation, increase the efficacy of an alkylating agent, and/or increase neoplastic cell death. One skilled in the art appreciates that the effects of a candidate agent on a cell is typically compared to a corresponding control cell not contacted with the candidate agent. Thus, the screening methods include comparing the proliferation of a neoplastic cell contacted by a candidate agent to the proliferation of an untreated control cell.

In other embodiments, the expression or activity of APE1 in a cell treated with a candidate agent is compared to untreated control samples to identify a candidate compound that decreases the expression or biological activity of a APE1 polypeptide in the contacted cell. Polypeptide expression or activity can be compared by procedures well known in the art, such as Western blotting, flow cytometry, immunocytochemistry, binding to magnetic and/or APE1-specific antibody-coated beads, in situ hybridization, fluorescence in situ hybridization (FISH), ELISA, microarray analysis, RT-PCR, Northern blotting, or colorimetric assays, such as the Bradford Assay and Lowry Assay.

In one working example, one or more candidate agents are added at varying concentrations to the culture medium containing a neoplastic cell. An agent that binds in an APE1 endonuclease site of APE or that reduces the expression or activity of a APE1 protein expressed in the cell is considered useful in the invention; such an agent may be used, for example, as a therapeutic to prevent, delay, ameliorate, stabilize, or treat a neoplasia. Once identified, agents of the invention (e.g., agents that specifically bind to and/or antagonize APE1) may be used to treat a neoplasia. An agent identified according to a method of the invention is locally or systemically delivered to treat a neoplasia in situ.

If one embodiment, the effect of a candidate agent may, in the alternative, be measured at the level of APE1 polypeptide production using the same general approach and standard immunological techniques, such as Western blotting or immunoprecipitation with an antibody specific for APE1. For example, immunoassays may be used to detect or monitor the expression of APE1 in a neoplastic cell. In one embodiment, the invention identifies a polyclonal or monoclonal antibody (produced as described herein) that is capable of binding to a APE1 endonuclease site and reducing the biological activity of a APE1 polypeptide. A compound that reduces the expression or activity of a APE1 polypeptide is considered particularly useful. Again, such an agent may be used, for example, as a therapeutic to prevent or treat a neoplasia.

Alternatively, or in addition, candidate compounds may be identified by first assaying those that specifically bind to and antagonize a APE1 polypeptide of the invention and subsequently testing their effect on neoplastic cells as described in the Examples. In one embodiment, the efficacy of a candidate agent is dependent upon its ability to interact with the APE1 polypeptide. Such an interaction can be readily assayed using any number of standard binding techniques and functional assays (e.g., those described in Ausubel et al., supra). For example, a candidate compound may be tested in vitro for interaction and binding with a polypeptide of the invention and its ability to modulate neoplastic cell proliferation may be assayed by any standard assays (e.g., those described herein). In one embodiment, division of neoplastic cells is determined by assaying BrdU incorporation using flow cytometry analysis. In another embodiment, APE1 expression is monitored immunohistochemically.

Potential APE1 antagonists include organic molecules, peptides, peptide mimetics, polypeptides, nucleic acid ligands, aptamers, and antibodies that bind to a APE1 polypeptide and reduce its activity. In one particular example, a candidate compound that binds to a APE1 polypeptide may be identified using a chromatography-based technique. For example, a recombinant APE1 polypeptide of the invention may be purified by standard techniques from cells engineered to express the polypeptide, or may be chemically synthesized, once purified the peptide is immobilized on a column. A solution of candidate agents is then passed through the column, and an agent that specifically binds the APE1 polypeptide or a fragment thereof is identified on the basis of its ability to bind to APE1 polypeptide and to be immobilized on the column. To isolate the agent, the column is washed to remove non-specifically bound molecules, and the agent of interest is then released from the column and collected. Agents isolated by this method (or any other appropriate method) may, if desired, be further purified (e.g., by high performance liquid chromatography). In addition, these candidate agents may be tested for their ability to reduce neoplastic cell proliferation or viability. Agents isolated by this approach may also be used, for example, as therapeutics to treat or prevent a neoplasia. Compounds that are identified as binding to a APE1 polypeptide with an affinity constant less than or equal to 1 nM, 5 nM, 10 nM, 100 nM, 1 µM or 10 µM are considered particularly useful in the invention.

Test Compounds and Extracts

In general, APE1 antagonists (e.g., agents that specifically bind and reduce the activity of a APE1 polypeptide) and other agents that enhance the efficacy of an agent described herein are identified from large libraries of natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Agents used in screens may include known those known as therapeutics for the treatment of a neoplasia. Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223, 409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222: 301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have APE1 binding activity further fractionation of the positive lead extract is necessary to isolate molecular constituents responsible for the observed effect. Thus, the goal of the extraction, fractionation, and purification process is the careful characterization and identification of a chemical entity within the crude extract that reduces neoplastic cell proliferation or viability. Methods of fractionation and purification of such heterogenous extracts are known in the art. If desired, compounds shown to be useful as therapeutics are chemically modified according to methods known in the art.

Pharmaceutical Therapeutics

In other embodiments, agents discovered to have medicinal value using the methods described herein are useful as a drug or as information for structural modification of existing compounds, e.g., by rational drug design. Such methods are useful for screening agents having an effect on a neoplasia.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia.

Generally, amounts will be in the range of those used for other agents used in the treatment of other diseases associated with neoplasia, although in certain instances lower amounts will be needed because of the increased specificity of the compound. A compound is administered at a dosage that is cytotoxic to a neoplastic cell, that reduces APE1 expression or biological activity, or that reduces the proliferation, survival, or invasiveness of a neoplastic cell as determined by a method known to one skilled in the art, or using any that assay that measures the expression or the biological activity of a APE1 polypeptide.

Formulation of Pharmaceutical Compositions

The administration of a compound or a combination of compounds for the treatment of a neoplasia may be by any suitable means that results in a concentration of the therapeutic that, combined with other components, is effective in ameliorating, reducing, or stabilizing a neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 µg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other embodiments, it is envisaged that doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active antineoplastic therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate).

In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

Solid Dosage Forms for Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active anti-neoplasia therapeutic substance). The coating may be applied on the solid dosage form in a similar manner as that described in Encyclopedia of Pharmaceutical Technology, supra.

At least two anti-neoplasia therapeutics may be mixed together in the tablet, or may be partitioned. In one example, the first active anti-neoplasia therapeutic is contained on the inside of the tablet, and the second active anti-neoplasia therapeutic is on the outside, such that a substantial portion of the second anti-neoplasia therapeutic is released prior to the release of the first anti-neoplasia therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the active anti-neoplasia therapeutic by controlling the dissolution and/or the diffusion of the active substance. Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more therapeutic compounds may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

The present invention provides methods of treating neoplastic disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a neoplastic disease or disorder or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a neoplastic disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which APE1 may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Selection of a Treatment Method

After a subject is diagnosed as having a neoplasia (e.g., pancreatic cancer, colon cancer, and brain cancer, such as glioblastoma) a method of treatment is selected. In pancreatic cancer, for example, a number of standard treatment regimens are available. In general, pancreatic cancers are one of the most aggressive forms of cancer, and advanced pancreatic cancers are rarely susceptible to conventional treatment methods. For aggressive pancreatic cancer, few therapeutic options are available, and such tumors often correlate with poor clinical outcomes, such as metastasis or death. A subject having aggressive pancreatic cancer is identified as likely to benefit from treatment with a composition of the invention comprising cisplatin, gemcitabine, and NSC-30049. Thus, the invention provides methods for selecting a therapy for a subject, the method involving identifying a subject as having aggressive neoplasia, such as pancreatic cancer, or aggressive forms of colon cancer or glioblastoma, and administering to the subject a therapeutic combination of the invention.

Even when a subject with neoplasia (e.g., pancreatic cancer, colon cancer, and brain cancer, such as glioblastoma) is identified as having a good clinical outcome, the subject is also likely to benefit from treatment with the methods of the invention (e.g., lower side effects). When methods of the invention indicate that a neoplasia is very aggressive, an aggressive method of treatment should be selected. Aggressive therapeutic regimens typically include one or more of the following therapies: radical mastectomy, radiation therapy, hormone therapy, and chemotherapy. Such methods may be used in combination with the therapeutic methods described herein, particularly for the treatment of pancreatic cancer, which is prone to relapse.

Methods of Treatment

In one embodiment, the present invention provides a method of treating neoplasia (e.g., pancreatic cancer, colon cancer, and brain cancer, such as glioblastoma). Advantageously, the invention provides methods for treating neoplasia (e.g., pancreatic cancers, colon cancer, and brain cancer, such as glioblastoma) that are less susceptible to conventional treatment methods. The methods involve administering to a subject having a neoplasia an effective amount of a therapeutic combination of the invention. For example, a composition comprising an alkylating agent, such as cisplatin, a small molecule inhibitor, such as NSC-30049, together with gemcitabine or a chemopreventive agent. Preferably, such agents are administered as part of a composition additionally comprising a pharmaceutically acceptable carrier. Preferably this method is employed to treat a subject suffering from or susceptible to a neoplasia. Other embodiments include any of the methods herein wherein the subject is identified as in need of the indicated treatment.

Another aspect of the invention is the use of a combination of the invention in the manufacture of a medicament for treating a neoplasia (e.g., pancreatic cancer) in a subject. Preferably, the medicament is used for treatment or prevention in a subject of a disease, disorder or symptom set forth above.

Kits or Pharmaceutical Systems

The present compositions may be assembled into kits or pharmaceutical systems for use in ameliorating a neoplasia (e.g., pancreatic cancer, colon cancer, and brain cancer, such as glioblastoma). Kits or pharmaceutical systems according to this aspect of the invention comprise a carrier means, such as a box, carton, tube or the like, having in close confinement therein one or more container means, such as vials, tubes, ampoules, bottles and the like. The kits or pharmaceutical systems of the invention may also comprise associated instructions for using the agents of the invention. Kits of the invention include at least one or more alkylating agents (e.g., cisplatin, and at least one or more agents that bind to an APE1 endonuclease site or that reduce APE1 or BER pathway activity (e.g., NSC-30049). If desired, the kit also includes an agent that binds to ribonucleotide reductase (RR) and reduces nucleotide synthesis (e.g., gemcitabine). The kit may include instructions for administering the alkylating agent in combination with one or more agents that bind to an APE1 endonuclease site or that reduce APE1 or BER pathway activity (e.g., NSC-30049), thereby increasing the efficacy of the alkylating agent relative to the efficacy of the alkylating agent administered alone. Methods for measuring the efficacy of alkylating agents are known in the art and are described herein (e.g., measuring the $IC_{50}$).

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Structure-Based Docking of NSC-30049 at Amino Acid Residues E96, Y171, D210, N212, F266, W280, L282 and D308 of DNA Polymerase β (APE1)

Many chemotherapeutic drugs are DNA-alkylating agents and their efficacy can be improved by targeting specific DNA repair pathways, especially since DNA repair blockade causes accumulation of DNA damage and increases the sensitivity of the cells to these agents. The DNA-alkylating agent, Cisplatin, causes the formation of abasic (AP)-DNA lesions at $N^7$ position of adenine ($N^7$—PtA) (Pt, platinum) and guanine ($N^7$—Pt-G) (2-5) as well as intrastrand and interstrand Pt-DNA adducts (6). CISPLATIN treatment also generates reactive oxygen species (ROS), which produces oxidative DNA lesions (AP-lesions, single-strand DNA breaks, sugar moiety modifications and deaminated and adducted bases). The intrastrand and interstrand breaks are repaired by nucleotide excision repair (NER) pathway (47). The AP-lesions are repaired by base excision repair (BER) pathway, in which apurinic/apyrimidinic endonuclease 1 (APE1) plays a rate-limiting role (10). Accumulation of unrepaired AP-lesions due to defective BER can lead to apoptosis and enhanced cytotoxicity (48). On the other hand, increased expression of the BER pathway proteins in cancer cells can result in efficient repair of AP-lesions and can increase the resistance and reduce the effectiveness of chemotherapeutic agents (49). It has been shown that the increased level of APE1 confers resistance to Cisplatin treatment and also it serves as a prognostic factor in pancreatic cancer (13). Thus, manipulating the activity of APE1 in the BER pathway can be an attractive target for increasing the therapeutic efficacy and decreasing the doses of CISPLATIN to pancreatic cancer cells. The reduced dose of CISPLATIN will reduce or eliminate CISPLATIN treatment-associated side effects (28-32).

Figure 2:
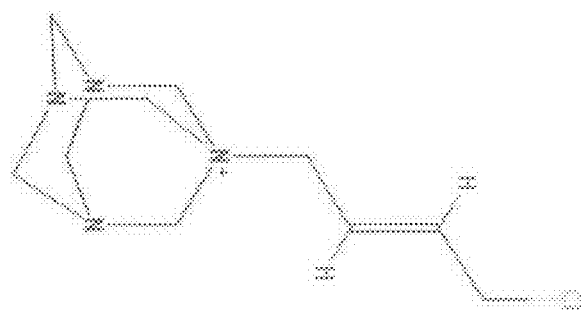
FIGS. 2A and 2B depict the chemical structure of NSC-30049 (Chemical formula: $C_{10}H_{18}Cl_2N_4$ {1-(4-Chloro-2-butenyl)-1.lambda.~5~,3,5,7-tetraazatricyclo[3.3.1.1~3,7~] decane}; Molecular weight: 264.73) and its derivatives.
Figure 2:
Figure 2:
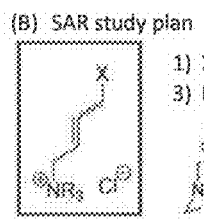
Figure 2:
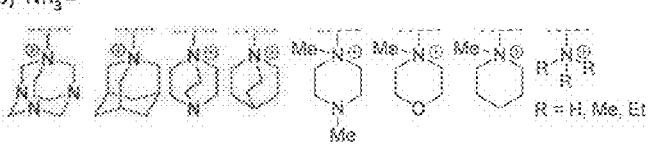

The catalytic domain of Apurinic/apyrimidinic (AP) endonuclease was modeled for binding of small molecule inhibitors (SMI). Small molecule inhibitors that target the catalytic pocket of APE1 were expected to block endonuclease activity of APE1 and APE1-directed BER. A library of 140,000 agents (Developmental and Therapeutics Program at NCI/NIH) was screened to identify those that are likely to bind at a catalytic pocket, including amino acid residues E96, Y171, D210, N212, F266, W280, L282, and D308 of APE1, and block its activity. NSC-30049 was identified as binding to the catalytic pocket (FIG. 1). The chemical formula of NSC-30049 is {1-(4-Chloro-2-butenyl)-1.lambda.~5~,3,5,7-tetraazatricyclo[3.3.1.1~3,7~]decane)} (FIG. 2). NSC-30049 exhibited a docking score of 50.9657 kcal/mol.

Figure 3:
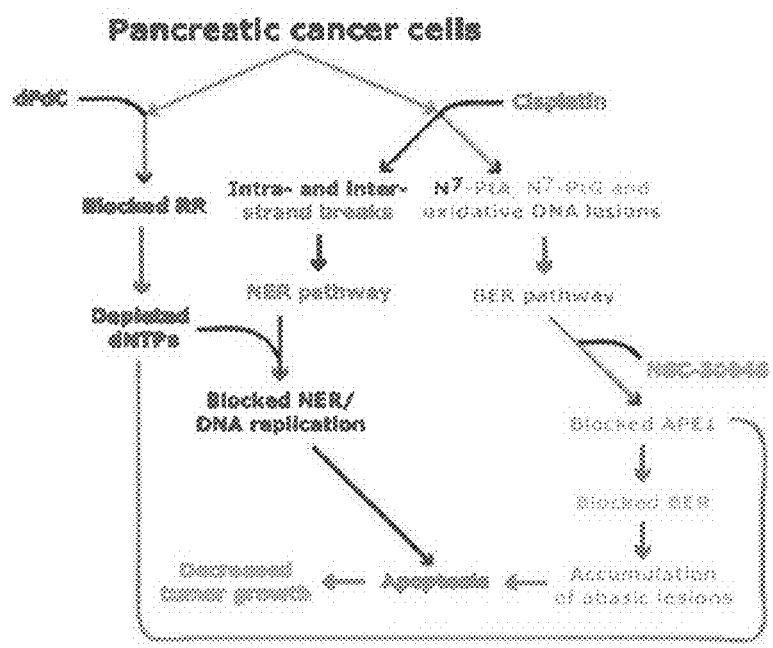
FIG. 3 depicts a model in which NSC-30049-mediated block of APE1 activity/base excision repair (BER) pathway and gemcitabine (dFdC)-mediated block of nucleotide excision repair (NER)/BER/DNA replication pathways increases the sensitivity of pancreatic cancer cells to cisplatin (CDDP). Pt-A, platinum-adenine; Pt-G, platinum-guanine; RR, ribonucleotide reductase.

Because APE1 performs an essential function in DNA base-excision repair pathway, it is a target for preventing cancer cells from surviving chemotherapy. Without being bound to a particular theory, NSC-30049 mediates a block of APE1 activity/BER pathway and dFdC-mediated block of DNA repair/replication pathways (FIG. 3). Downstream signaling to DNA damage is linked to the deregulation of miRNAs and activation of apoptosis to synergize the sensitivity of CDDP and dFdC in pancreatic cancer cells.

Example 2

NSC-30049 Blocked APE1-Mediated BER

Figure 4:
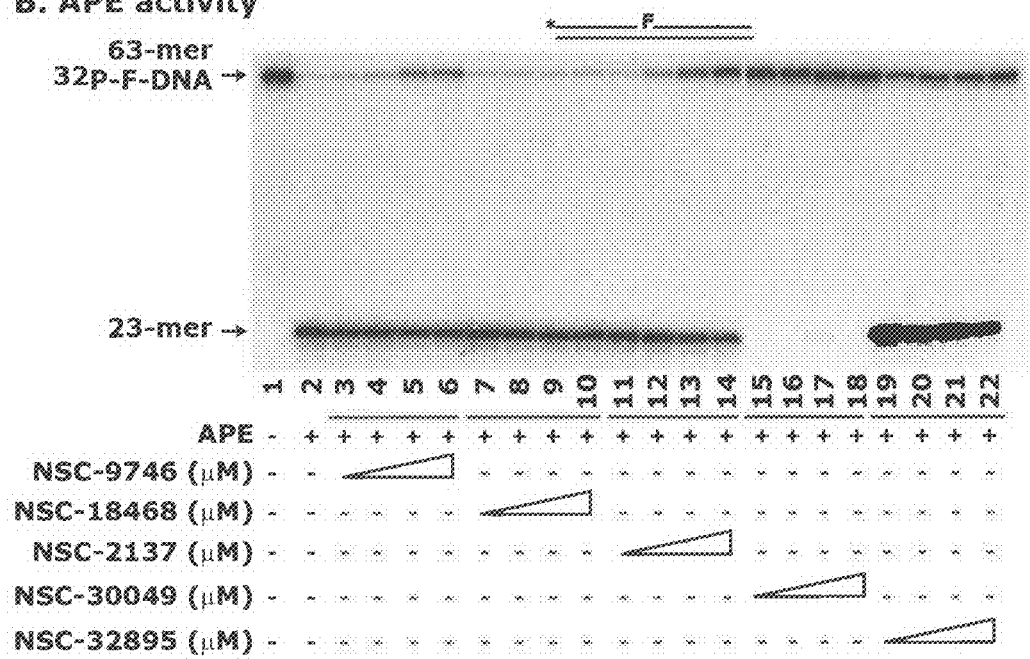
FIGS. 4A and 4B depict the screening of small molecules.

To determine the effect of compounds on the blockage of APE1 activity, an in vitro assay system was developed using purified APE1 and $^{32}$P-labeled 63-mer F-DNA (FIG. 4A). Several small molecules (NSC-9746, NSC-18468, NSC-2137, NAC-30049 and NSC-32895) were screened for their ability to inhibit APE1 activity in the in vitro assay (FIG. 4B). Of these compounds, NSC-30049 to inhibit APE1 activity in the in vitro assay at all concentrations tested (5, 10, 20 and 40 µM).

Figure 5:
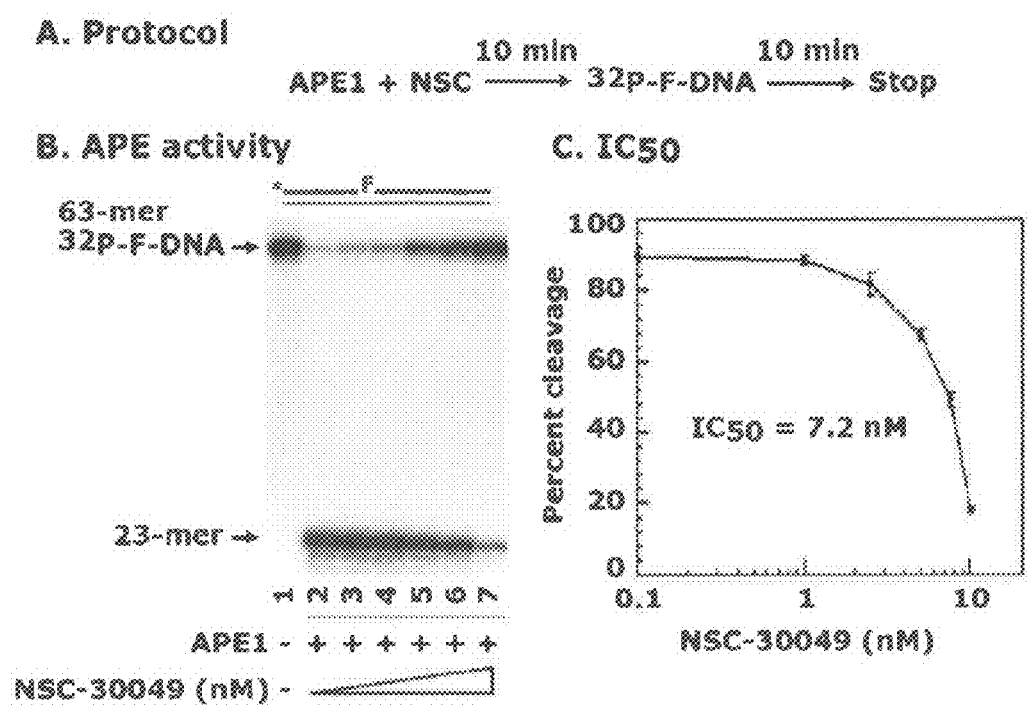
FIGS. 5A-5C show that NSC-30049 blocks APE1 activity.
Figure 6:
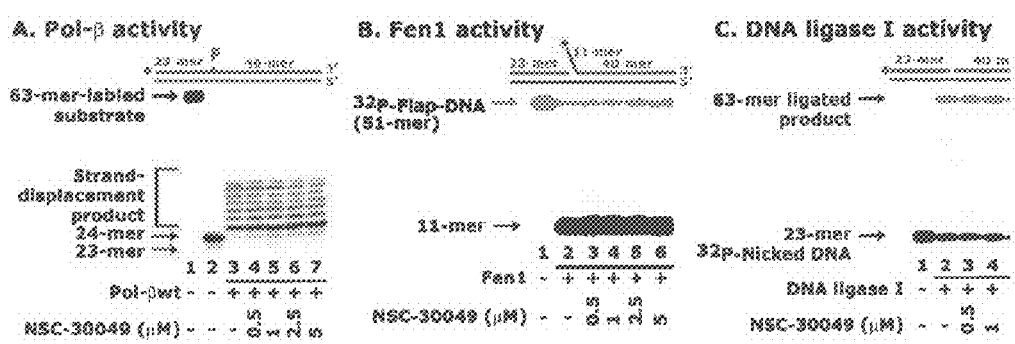
FIGS. 6A-6C show that NSC-30049 does not block the activity of Pol-β, Fen1, and DNA ligase 1 in reconstituted in vitro assays.
Figure 7:
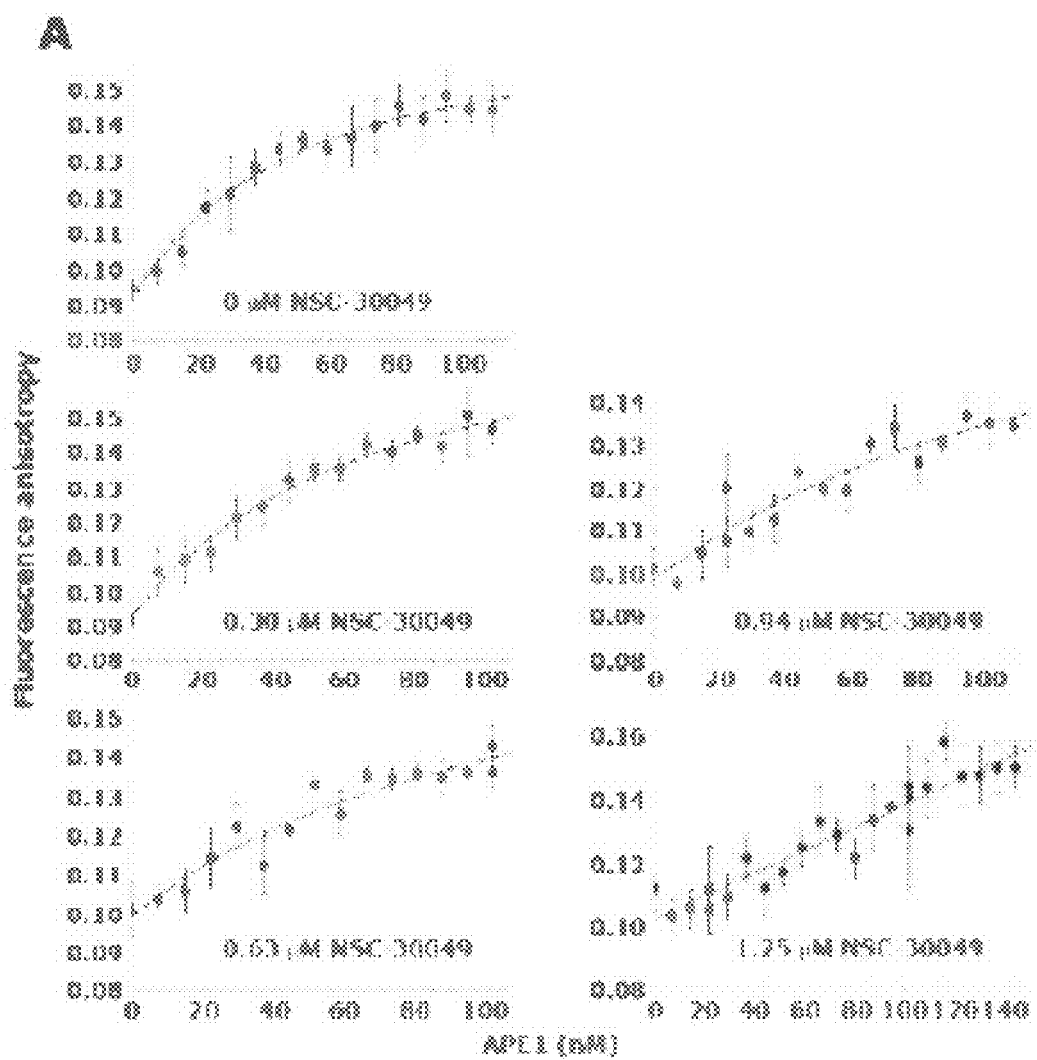
FIGS. 7A and 7B show the effect of NSC-30049 on the APE1 affinity for AP-lesion containing DNA.

The small molecule inhibitor (SMI), NSC-30049, was identified as an inhibitor of APE1 endonuclease activity by molecular docking. NSC-30049 was readily soluble in water and specifically interacted with and blocked the activity of APE1 in vitro in a dose-dependent manner and at very low concentrations (i.e., $IC_{50}$=7.2 nM) (FIGS. 5A-5C). APE1 did not affect the in vitro activity of other BER enzymes such as APE1, Fen1, and DNA ligase I (FIGS. 6A-6C). Using fluorescence anisotropy assays, NSC-30049 blocked the binding of APE1 with AP-site DNA in a dose-dependent manner (FIGS. 7A and 7B).

Without being bound to a particular theory, the inactivation of APE1 (to block BER activity) by SMI (e.g., NSC-30049) enhances the therapeutic efficacy of cisplatin. Moreover, without being bound to a particular theory, the combination of SMI (e.g., NSC-30049) and an RR inhibitor (gemcitabine) (to block NER/BER/DNA replication) further reduces the dose of cisplatin and potentiates its therapeutic efficacy. Importantly, the resistance caused by gemcitabine in pancreatic cancer cell lines is removed by combination with NSC-30049 (Tables 1 and 2), which is an important development for combatting pancreatic cancer.

TABLE 1

$IC_{50}$ of NSC-30049 and dFdC in dFdC-resistant and dFdC-sensitive pancreatic cancer cell lines.

| | NSC-30049 ($IC_{50}$ µM) | dFdC ($IC_{50}$ µM) |
|---|---|---|
| dFdC-resfstant | | |
| AsPC1 | 1.88 ± 0.11 | 1.83 ± 0.47 |
| PANC1 | 5.12 ± 0.22 | 11.63 ± 2.93 |
| Mia-PaCa2 | 5.12 ± 0.22 | 11.54 ± 2.90 |

TABLE 1-continued

IC$_{50}$ of NSC-30049 and dFdC in dFdC-resistant and dFdC-sensitive pancreatic cancer cell lines.

| | NSC-30049 (IC$_{50}$ µM) | dFdC (IC$_{50}$ µM) |
|---|---|---|
| dFdC-sensitive | | |
| BxPC3 | 3.87 ± 0.24 | 0.07 ± 0.005 |
| HPAC | 4.44 ± 0.28 | 0.07 ± 0.007 |

Cells were treated with different concentrations of drugs for 72 h and then processed for MTT assay. Data is representative of mean ± SE of three different experiments.

TABLE 2

The combination of NSC-30049 and/or dFdC treament synergistically reduces the IC50 of CDDP in both dFdC-resistant and dFdC-sensitive pancreatic cancer cell lines.

| | dFdC-resistant | | | dFdC-sensitive | |
|---|---|---|---|---|---|
| | AsPC1 | PANC1 | Mia-PaCa2 | BxPC3 | HPAC |
| NSC-30049 (µM) | | No dFdC | CDDP (IC$_{50}$ µM) | No dFdC | |
| 0 | 3.49 ± 0.13 | 9.55 ± 0.94 | 22.27 ± 1.10 | 1.96 ± 0.08 | 14.07 ± 4.34 |
| 0.5 | 2.20 ± 0.22 | 9.00 ± 0.03 | 14.29 ± 0.49 | 1.53 ± 0.09 | 14.54 ± 2.47 |
| 1.0 | 2.09 ± 0.19 | 7.80 ± 0.50 | 13.44 ± 1.33 | 1.38 ± 0.04 | 11.63 ± 1.82 |
| 2.5 | 0.20 ± 0.01 | 2.04 ± 0.41 | 12.20 ± 1.12 | 0.26 ± 0.07 | 4.71 ± 1.24 |
| NSC-30049 (µM) | | 1 µM dFdC | | 0.025 µM dFdC | |
| 0 | 3.19 ± 0.28 | 9.87 ± 0.80 | 22.20 ± 1.15 | 2.02 ± 0.35 | 13.77 ± 5.51 |
| 0.5 | 0.64 ± 0.08 | 1.06 ± 0.39 | 0.09 ± 0.00 | 0.94 ± 0.06 | 0.02 ± 0.01 |
| 1.0 | 0.11 ± 0.09 | 1.03 ± 0.36 | 0.07 ± 0.00 | 0.54 ± 0.06 | 0.01 ± 0.001 |
| 2.5 | 0.004 ± 0.0001 | 0.12 ± 0.09 | 0.07 ± 0.00 | 0.04 ± 0.001 | 0.01 ± 0.001 |

Cells were pre-treated for 2 h with different concentrations of NSC-30049 alone or in combination with dFdC (1 and 0.25 µM to dFdC-resistant and dFdC-sensitive cell lines, respectively) followed by the treatment with different concentrations of CDDP. After 72 h of the drug treatment, cells were processed for MTT assay. Data is representative of mean ± SE of three different experiments.

NSC-30049 in combination with oxaliplatin was also effective in inhibiting the growth of pancreatic colon cancer cell lines in culture (BxPC3 and PANC1) (Table 3).

TABLE 3

Effect of NSC-30049 on oxaliplatin-mediated cell growth inhibition of pancreatic colon cancer cell lines in culture.

IC$_{50}$ of Oxaliplatin (µM)

| NSC-30049 (µM) | 0 | 0.5 | 1.0 | 2.5 |
|---|---|---|---|---|
| BxPC3 | 2.0 ± 0.4 | 0.71 ± 0.39 | 0.33 ± 0.06** | 0.01 ± 0.00*** |
| PANC1 | 14.5 ± 0.38 | 0.38 ± 0.06*** | 0.13 ± 0.04*** | 0.37 ± 0.22*** |

Cells were pre-treated for 2 h with 0.5, 1.0, and 2.5 µM of NSC-30049 prior to treatment with oxaliplatin (OPT). After the treatment cells were allowed to grow for 48 h and cell growth inhibition was determined by MTT assay. Data presented are the mean ± SE of three different estimations. The p value as compared to control of the Student's t-test is given in parenthesis.
**p < 0.01;
***p < 0.001, Example 3

Figure 8:
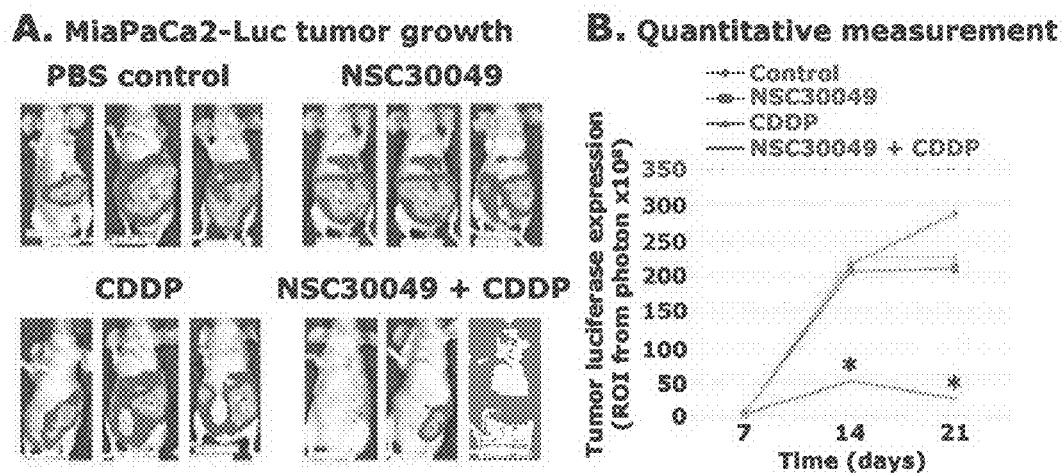
FIGS. 8A and 8B show that NSC-30049 treatment synergistically increases the chemotherapeutic efficacy of CDDP in vivo.

NSC-30049 Administered in Combination with Cisplatin Reduced Tumor Growth in a Mouse Model of Pancreatic Cancer In models of tumor growth in athymic mice using the pancreatic cancer cell line MiaPaCa2-Lu, NSC-30049 treatment synergistically increased the chemotherapeutic efficacy of CDDP in vivo (FIG. 8A). A synergistic effect on the inhibition of MiaPaCa2-Lu tumor growth was observed after combination treatment of NSC-30049 and CDDP, as measured by tumor luciferase expression (FIG. 8B).

Thus, NSC-30049 when administered in combination with cisplatin was effective in treating tumor growth in a model of pancreatic cancer.

Example 4

NSC-30049 Administered in Combination with Temozolomide or Oxaliplatin Reduced Growth of Colon Cancer Cells in Culture The use of NSC-30049 as a chemopreventive agent for the treatment of colon cancer was also tested. In one experiment, NSC-30049 in combination with temozolomide was administered to colon cancer cell lines, including mismatch repair (MMR) proficient and MMR deficient cancer cell lines (Table 4). MMR proficient colon cancer cell lines tested included HCT-116+ch3, SW480, and HT29. MMR deficient cancer cell lines tested included HCT-116 and LoVo. Cells were pre-treated for 2 h with 0.5, 1.0, 2.5 and 5 M concentrations of NSC-30049 prior to treatment with temozolomide. After the treatment cells were allowed to grow for 72 hours. The cell growth inhibition was determined by MTT assay. Data presented are the mean±SE of three different estimations. The p value as compared to control of the Student's t-test is given in parenthesis. * p<0.05;  p<0.01; * p<0.001. Increasing the concentration of NSC-30049 decreased the IC$_{50}$ of temozolomide for all cell lines tested, regardless of whether they were MMR proficient or deficient.

Thus, NSC-30049 when administered in combination with temozolomide resulted in increased sensitivity of colon cancer cells to temozolomide.

TABLE 4

Effect of NSC-30049 on temozolomide-mediated cell growth inhibition
of MMR-proficient and MMR-deficient colon cancer cell lines in culture.

IC$_{50}$ of TMZ (µM)

| NSC-30049 (µM) | 0 | 0.5 | 1.0 | 2.5 | 5.0 |
|---|---|---|---|---|---|
| MMR-proficient | | | | | |
| HCT-116 + ch3 | 236 ± 23 | 206 ± 13 | 153 ± 10* | 0.73 ± 0.04*** | 0.35 ± 0.01*** |
| SW480 | 377 ± 12 | 325 ± 18 | 167 ± 49* | 0.47 ± 0.03*** | |
| HT29 | 1454 ± 144 | 1270 ± 60 | 815 ± 93* | 248 ± 59** | 5.33 ± 0.07*** |
| MMR-deficient | | | | | |
| HCT-116 | 620 ± 11 | 361 ± 10*** | 160 ± 63** | 3.81 ± 0.11*** | |
| LoVo | 1106 ± 0.02 | 366 ± 6*** | 8 ± 0.8*** | 3.82 ± 0.09*** | |

In addition to temozolomide, oxaliplatin is another chemotherapeutic agent used for the treatment of colon cancer. In another experiment, NSC-30049 in combination with oxaliplatin was administered to colon cancer cell lines, including mismatch repair (MMR) proficient and MMR deficient cancer cell lines (Table 5). MMR proficient colon cancer cell lines tested included HCT-116+ch3 and HT29. MMR deficient cancer cell lines tested included HCT-116 and LoVo. Cells were pre-treated with the indicated concentrations of NSC-33049 for 2 h followed by the treatment with different concentrations of oxaliplatin for additional 48 h. The cell growth inhibition was determined by MTT assay. Data presented are the mean±SE of three different estimations. The p value of Student's t-test as compared to the control is given in parenthesis (* p<0.05;  p<0.01; * p<0.001). Increasing the concentration of NSC-30049 decreased the IC$_{50}$ of oxaliplatin for all cell lines tested, regardless of whether they were MMR proficient or deficient.

Figure 9:
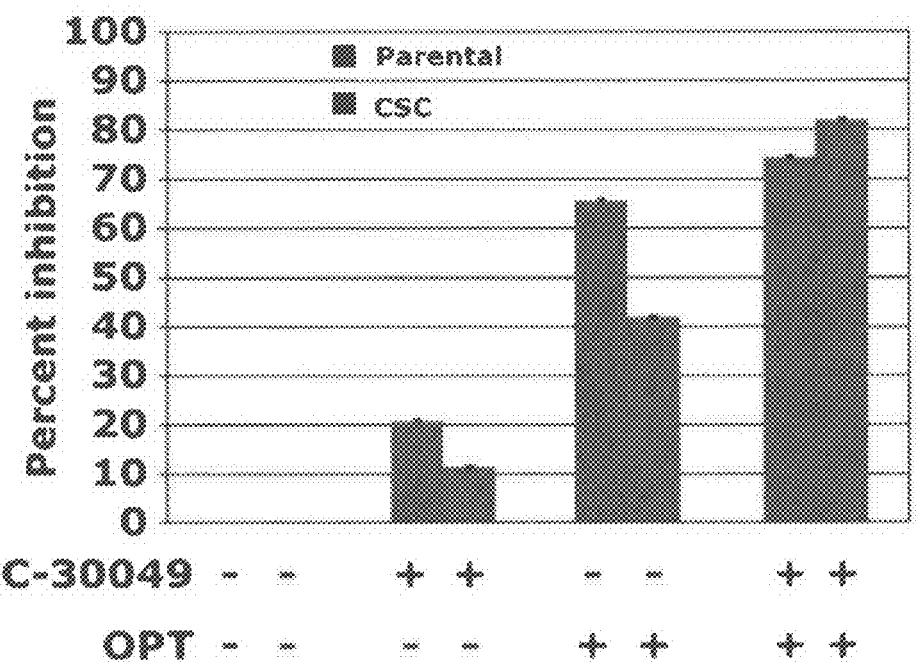
FIGS. 9A and 9B show that NSC-30049 in combination with oxaliplatin (OPT) inhibits growth and expression of self-renewal marker genes in colon cancer stem cells.
Figure 9:
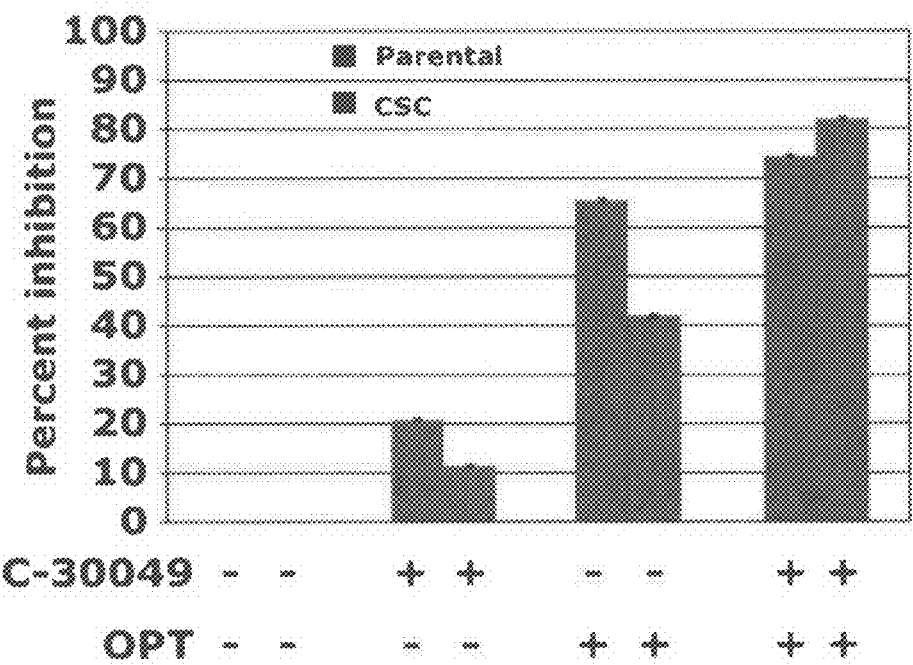

The effect of administration of NSC-30049 in combination with oxaliplatin (OPT) was also examined in human parental cancer cells and colon cancer stem cells (FIG. 9A). Cells were treated with 1.25 µM of NSC-30049 and 1.25 M of OPT either alone or in combination for 72 h. Cell growth inhibition was assayed. Data presented are mean±SD of triplicate experiments. NSC-30049 in combination with oxaliplatin (OPT) inhibited the growth of colon cancer stem cells ~80%, compared to either NSC-30049 alone (~10%) or oxaliplatin alone (~40%). In comparison, NSC-30049 in combination with oxaliplatin (OPT) inhibited the growth of human parental cancer cells ~70%, compared to either NSC-30049 alone (~20%) or oxaliplatin alone (~65%).

Without being bound to a particular theory, the effect of administration of NSC-30049 in combination with oxaliplatin (OPT) on the expression of self-renewal marker genes of colon cancer stem cells was analyzed. Self-renewal marker genes are highly expressed in colon cancer stem cells compared to human parental cancer cells. qRT-PCR data of CD133+, Oct4, Sox2 and Nanog gene expression levels of parental cancer cells and colon cancer stem cells was obtained (FIG. 9B). Cells were treated with 1.25 µM of NSC-30049 and 1.25 µM of OPT either alone or in combination for 72 h. The fold change in gene expression values is shown as mean±SD of three experiments and were normalized to GAPDH gene expression. The combination of NSC-30049 and oxaliplatin (OPT) significantly inhibited the expression of CD133, Nanog, Oct4, and Sox2 in colon cancer stem cells, compared to either NSC-30049 alone or oxaliplatin alone. In comparison, the combination of NSC-30049 and oxaliplatin (OPT) inhibited the expression of CD133, Nanog, Oct4, and Sox2 in human parental cancer cells, compared to either NSC-30049 alone or oxaliplatin alone. However, the reduction in normalized fold expression in human parental cancer cells was not to the same extent observed in the colon cancer stem cells.

Thus, NSC-30049 when administered in combination with oxaliplatin resulted in increased sensitivity of colon cancer cells to oxaliplatin and inhibited growth of colon cancer stem cells.

TABLE 5

Effect of NSC-30049 on Oxaliplatin-mediated cell growth inhibition
of MMR-proficient and MMR-deficient colon cancer cell lines in culture.

IC$_{50}$ of oxaliplatin (µM)

| NSC-30049 (µM) | 0 | 0.5 | 1.0 | 2.5 | 5.0 |
|---|---|---|---|---|---|
| MMR-proficient | | | | | |
| HCT-116 + ch3 | 5.83 ± 0.36 | | 4.98 ± 0.17 | 0.91 ± 0.12*** | 0.03 ± 0.00*** |
| HT29 | 0.92 ± 0.03 | | 0.82 ± 0.06 | 0.59 ± 0.02*** | 0.03 ± 0.0*** |
| MMR-deficient | | | | | |
| HCT-116 | 1.50 ± 0.01 | | 0.78 ± 0.02*** | 0.03 ± 0.0*** | 0.02 ± 0.0*** |
| LoVo | 0.75 ± 0.02 | 0.59 ± 0.04* | 0.07 ± 0.02*** | 0.03 ± 0.0*** | |

Example 5

Figure 10:
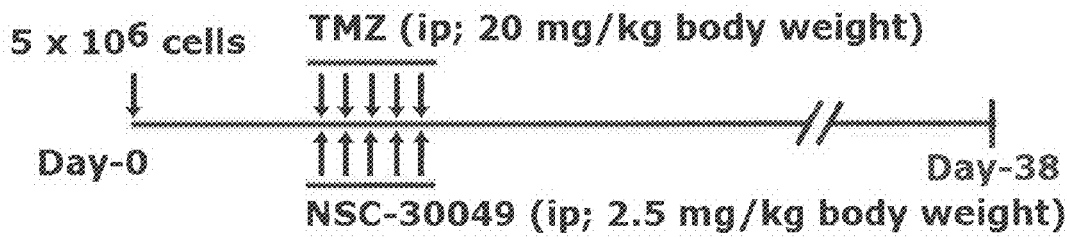
FIGS. 10A and 10B show that NSC-30049 in combination with TMZ inhibited growth of tumors in a xenograft model.
Figure 10:
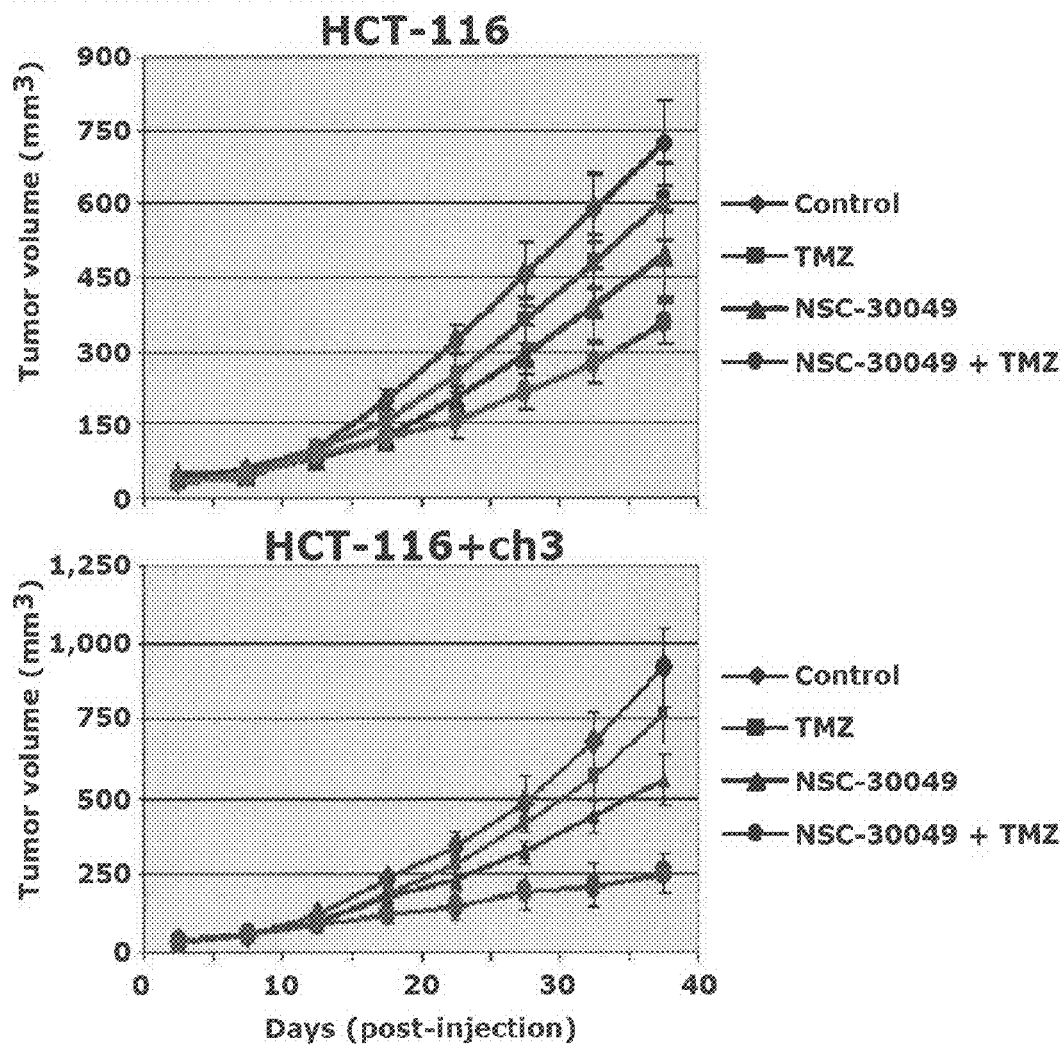

NSC-30049 Administered in Combination with Temozolmide Reduced Tumor Growth in a Xenograft Model of Colon Cancer Xenograft models of colon cancer were used to test the effect of NSC-30049 as a chemopreventive agent when administered in combination with temozolomide. A schematic representation of the experimental protocol is shown in FIG. 10A. At day 0, the xenograft host was administered with cells from a colon cancer cell line (HCT-116, MMR deficient; HCT-116+ch3, MMR proficient). Thereafter, temozolomide (20 mg/kg body weight; intraperitoneal) and/or NSC-30049 (2.5 mg/kg body weight; intraperitoneal) were administered to the animals. Tumor growth was evaluated at day 38.

In the xenograft models of colon cancer, a synergistic effect on the inhibition of tumor growth was observed after combination treatment of NSC-30049 and temozolomimde, as measured as measured by tumor volume (FIG. 10B). NSC-30049 treatment synergistically increased the chemotherapeutic efficacy of temozolomide regardless of whether the colon cancer cells were MMR proficient or deficient (FIG. 10B).

Thus, NSC-30049 when administered in combination with temozolomide was effective in treating tumor growth in models of colon cancer.

Example 6

NSC-30049 Administered in Combination with Temozolomide Reduced Viability of Brain Cancer Cells in Culture and in Spheroid Assay The use of NSC-30049 as a chemopreventive agent for the treatment of brain cancer was also tested. NSC-30049 in combination with temozolomide was administered to brain cancer cell lines, including U118, U138, U87MG, A172, and T98 cell lines (Table 6). Cells were pretreated with the indicated concentrations of NSC-30049 followed by TMZ for 120 h. After treatment, cells were processed for the determination of viability by cell proliferation assay (MTT assay). The data from the graph was used for the determination of $IC_{50}$, which is presented as the mean±SE of three different estimations. Increasing the concentration of NSC-30049 decreased the $IC_{50}$ of temozolomide for all cell lines tested, regardless of whether they were MMR proficient or deficient.

TABLE 6

Cell growth inhibition of brain cancer cell lines treated with NSC-30049 and Temozolomide for 120 hr.
$IC_{50}$ of TMZ (μM)

| NSC-30049 (μM) | U118 | U138 | U87MG | A172 | T98 |
|---|---|---|---|---|---|
| 0 | 136.5 ± 3.7 | 432.1 ± 19.1 | 492.9 ± 83.9 | 154.0 ± 6.8 | 554.1 ± 53.9 |
| 1.0 | 78.4 ± 1.3 | 277.9 ± 14.6 | 33.0 ± 5.1 | 89.5 ± 7.8 | 511.2 ± 14.7 |
| 2.5 | 14.5 ± 2.5 | 3.8 ± 0.4 | 19.9 ± 10.5 | 82.9 ± 5.1 | 381.6 ± 5.9 |
| 5.0 | 1.1 ± 03 | 0.8 ± 0.02 | 13.7 ± 8.5 | 75.1 ± 5.2 | 245.1 ± 8.7 |

TABLE 7

Cell growth inhibition of brain cancer cell lines treated with NSC-30049 for 120 h.
$IC_{50}$ of NSC-30049 (μM)

| U118 | U138 | U87MG | A172 | T98 |
|---|---|---|---|---|
| 2.6 ± 0.1 | 2.1 ± 0.1 | 5.6 ± 1.0 | 6.5 ± 0.3 | 10.1 ± 0.3 |

Cells were treated with varying concentrations of NSC-30049 for 120 h. After the treatment, cells were processed for the viability by cell proliferation assay (MTT assay).

The data from Table 7 was used for the determination of $IC_{50}$.

For spheroid assays, spheroid formation was initiated using GBM-U87 (established cell line) cancer-initiating cells or GBM-LO (freshly established from the primary glioblastoma tumor) cancer-initiating cells. Single cell suspension was prepared from brain spheroid GBM-U87MG or GBM-LO cells by trypsinization. For the spheroid assay, 1,000 single cells were plated in triplicate in a 12-well plate. Cells were pretreated with 2.5 μM of NSC30049 or 10 or 100 μM of TMZ alone or in combination with NSC-30049 for 168 h. Then, spheroids containing 4 or more cells were counted. Data presented are the mean±SE of three different estimations.

Figure 11:
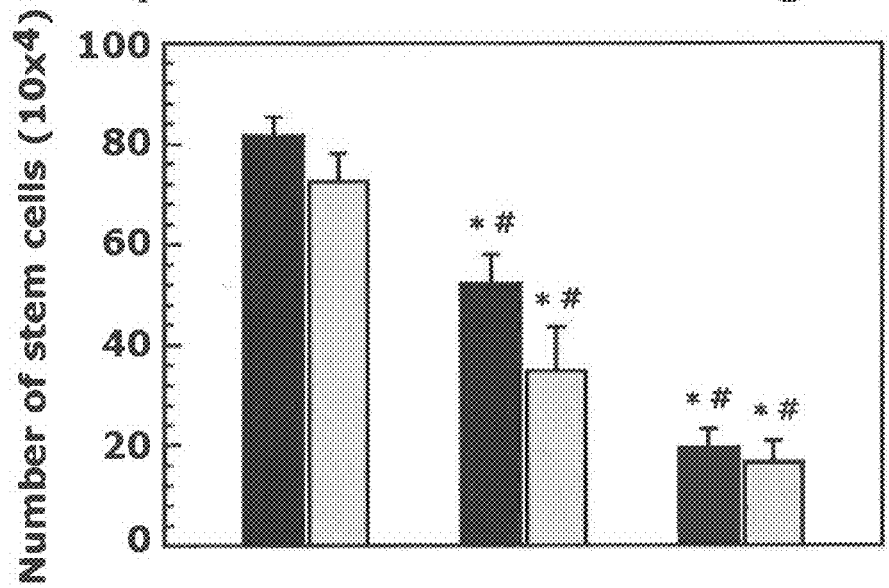
FIGS. 11A and 11B show that combination treatment of NSC-30049 with TMZ reduces the viability of cancer-initiating glioblastoma cell lines U87MG (established cell line) and GBM-LO (established freshly from the primary glioblastoma tumor).
Figure 11:
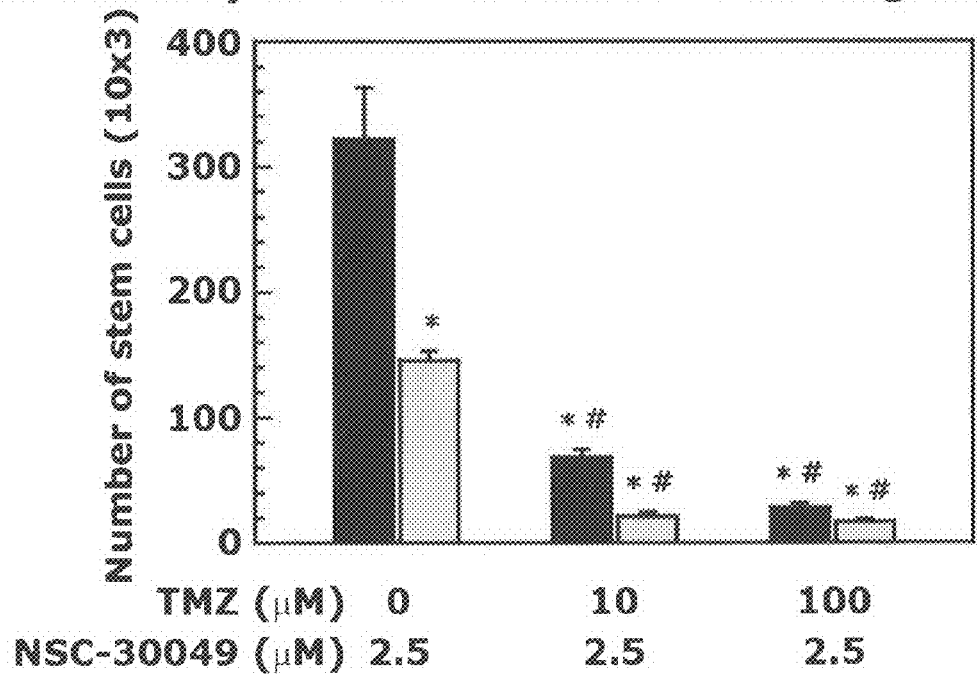
Figure 12:
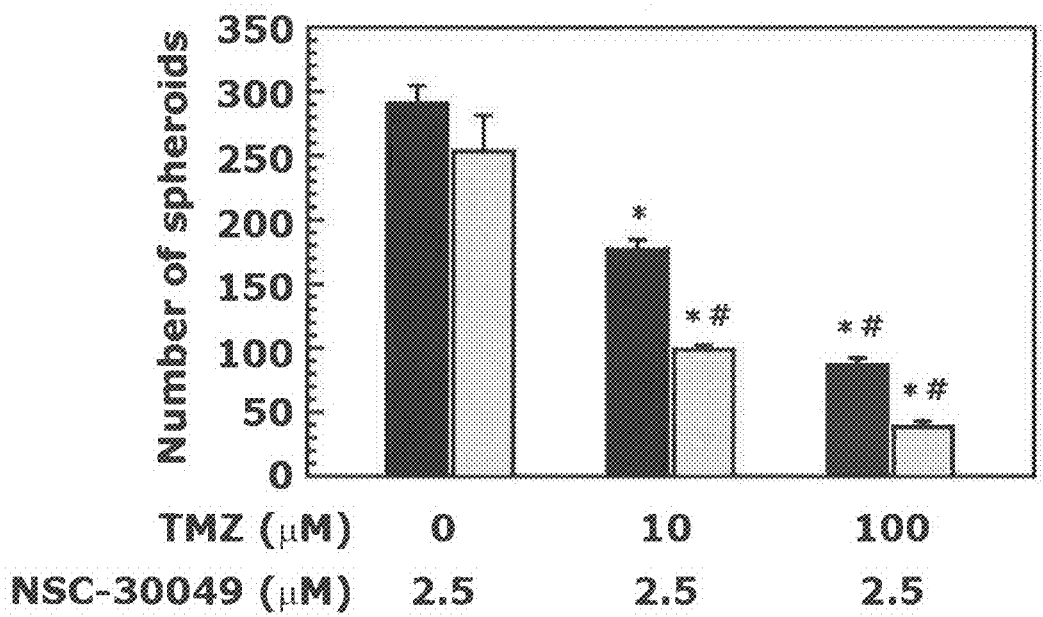
FIGS. 12A and 12B show that combination treatment of NSC-30049 with TMZ reduced spheroid formation activity of cancer-initiating glioblastoma cell line, U87MG.
Figure 12:
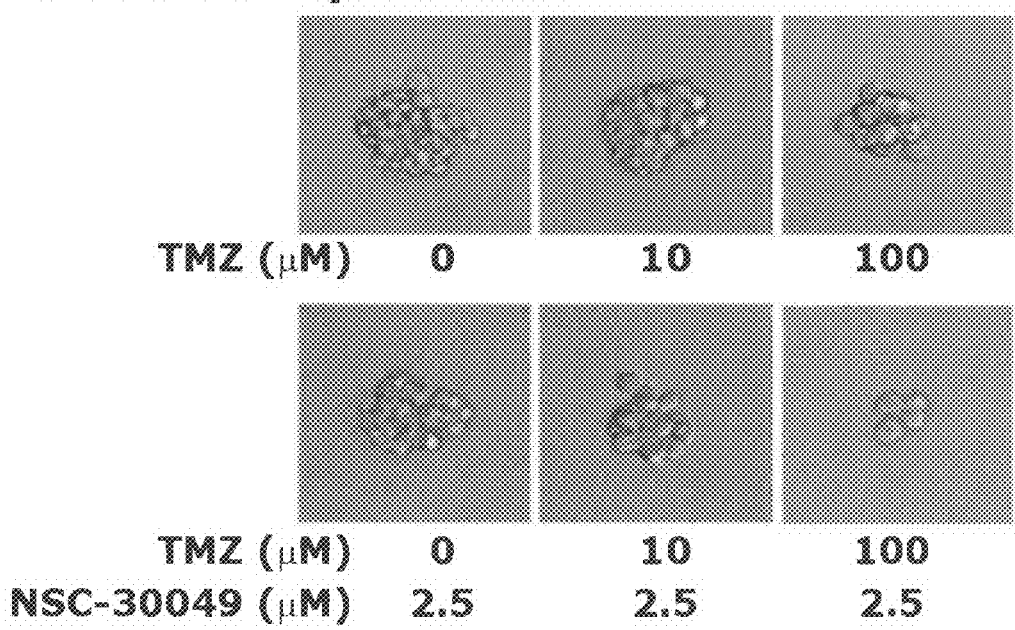
Figure 13:
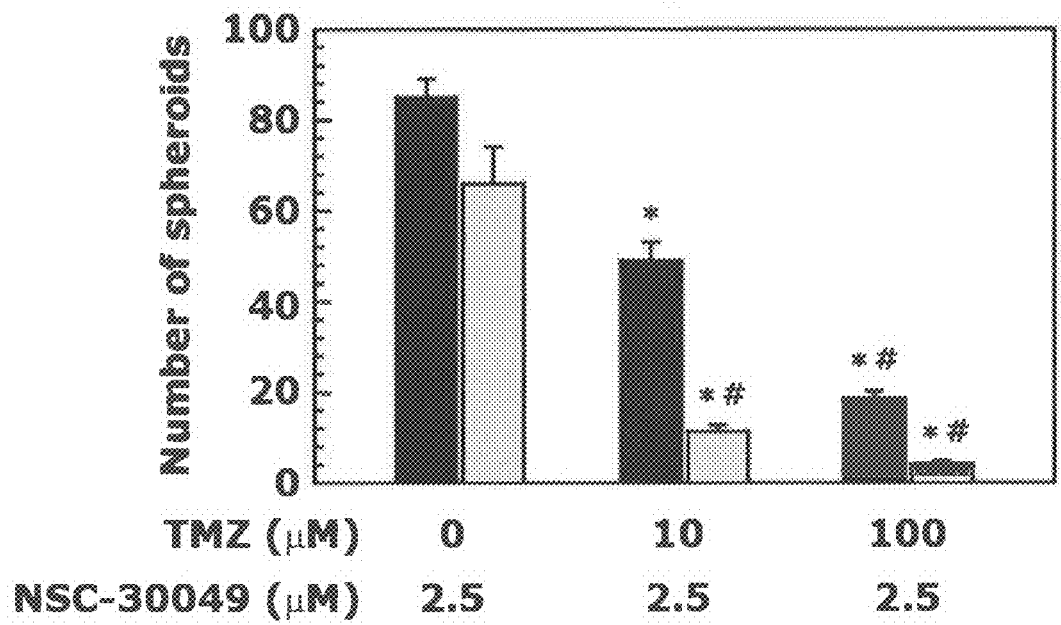
FIGS. 13A and 13B show that combination treatment of NSC-30049 with TMZ reduced spheroid formation activity of cancer-initiating glioblastoma cell line, GBM-LO.
Figure 13:
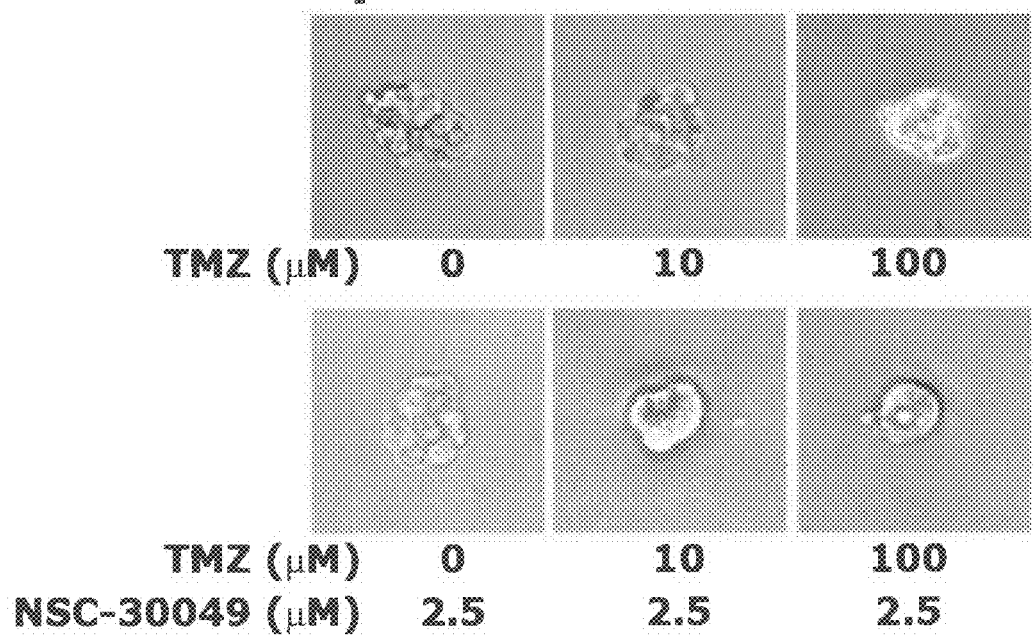

Treatment of GBM-U87 and GBM-LO spheroids with temozolomide alone and in combination with NSC-30049 decreased the viability of the cancer-initiating cells (FIGS. 11A and 11B). When temozolomide was administered in combination with NSC-30049, viability of cancer-initiating cells was reduced compared to temozolomide alone. The number of spheroids formed by both U87MG and GBM-LO cancer cell lines was also reduced when treated with temozolomide alone and in combination with NSC-30049 (FIGS. 12A and 13A). NSC-30049 increased the sensitivity of U87MG and GBM-LO spheroids to temozolomide. Spheroids treated with temozolomide and NSC-30049 showed fewer clustered cells than when temozolomide was administered alone (FIGS. 12B and 13B).

Figure 14:
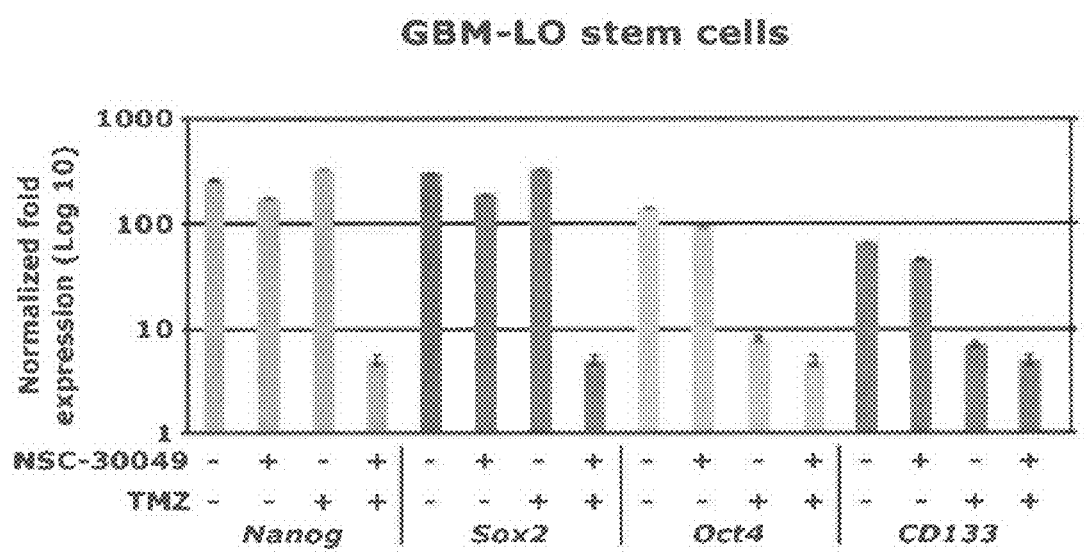
FIGS. 14A and 14B show that NSC-30049 in combination with oxaliplatin (OPT) inhibits growth and expression of self-renewal marker genes in colon cancer stem cells.
Figure 14:
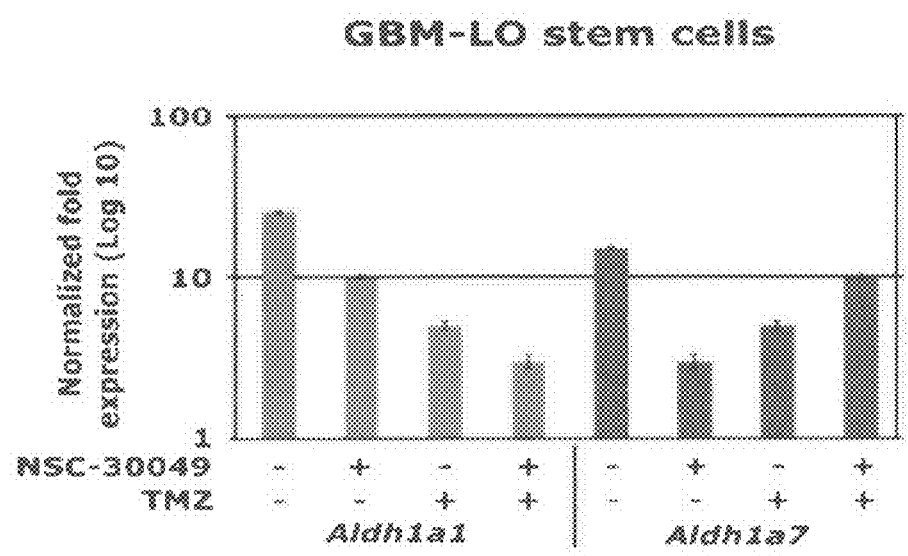

Without being bound to a particular theory, the effect of administration of NSC-30049 in combination with temozolomide (TMZ) on the expression of self-renewal marker genes of colon cancer stem cells was analyzed. Self-renewal marker genes are highly expressed in colon cancer stem cells compared to human parental cancer cells. qRT-PCR data of CD133+, Oct4, Sox2 and Nanog gene expression levels of GBM-L0 stem cells was obtained (FIG. 14A). Cells were pretreated with 2.5 μM of NSC30049 or 10 or 100 μM of TMZ alone or in combination with NSC-30049 for 36 h. Then, total RNA was isolated and processed for qRT-PCR. Data presented are the mean±SE of three different measurements. The combination of NSC-30049 and temozolomide significantly inhibited the expression of CD133, Nanog, Oct4, and Sox2 in GBM-L0 stem cells, compared to either NSC-30049 alone or temozolomide alone. qRT-PCR data of aldehyde dehydrogenase genes, Aldh1a1 and Aldh1a7 gene expression levels of GBM-L0 stem cells was obtained (FIG. 14B). Cells were pretreated with 2.5 µM of NSC30049 or 10 or 100 µM of TMZ alone or in combination with NSC-30049 for 36 h. Then, total RNA was isolated and processed for qRT-PCR. Data presented are the mean±SE of three different measurements. The combination of NSC-30049 and temozolomide significantly inhibited the expression of Aldh1a1 in GBM-L0 stem cells. Expression of Aldh1a7 in GBM-L stem cells was inhibited by either NSC-30049 alone or temozolomide alone, but not NSC-30049 and temozolomide.

Thus, NSC-30049 when administered in combination with temzolomide resulted in increased sensitivity of brain cancer cells to temozolomide and inhibited growth of brain cancer stem cells.

Example 7

NSC-30049 Derivatives that Inhibit APE1 Function

Potent derivatives are identified utilizing the validated route for the synthesized lead (NSC-30049) and functional testing of derivatives to construct a library of analogs from which structure activity relationships will be derived to reveal compounds with better potency. The validated route provides a sound basis for constructing a library of analogs of NSC-30049 from which structure activity relationship (SAR) can be derived to reveal compounds with better potency.

Changes to the structure of NSC-30049 are depicted in FIG. 2A. SAR is used to design further libraries of analogs. In general, the libraries are assembled in a modular fashion using standard modern techniques of parallel synthesis and purification. The libraries are designed to incorporate drug-like characteristics as described in the Lipinski guidelines (Log P, molecular weight, number of H-bond donors and acceptors etc.) to ensure suitable acceptable solubility and cellular availability. Once prepared and screened, emerging structure-activity data are used to direct consequent library design and selection of building blocks in an iterative fashion. Computational modeling software including GLIDE XP incorporating Quantum Polarized Ligand Docking (for high accuracy docking studies; Schrödinger, L.L.C.) and GOLD arrre used in lead optimization efforts to guide compound design and prioritization of compounds for chemical synthesis. The RACHEL (Real-time Automated Combinatorial Heuristic Enhancement of Lead compounds) program can also be used for automated combinatorial optimization of NSC-30049 by systematic derivatization of this molecule.

The lead compound and derivatives undergo testing to evaluate their ability to inhibit APE1 activity. A reconstituted assay system with purified UDG, APE-1, Pol-β, Fen-1 and DNA ligase I proteins is used to determine activity. The assay system is well-established as published in previous studies. $^{32}$P-U-DNA and $^{32}$P-F-DNA substrates are used to determine the effect of compounds on APE1 and base excision repair activities as previously described. Binding of a potent compound to APE1 is also confirmed by fluorescence anisotropy (FAN), and with biophysical methods including isothermal calorimetry or Biacore.

Using these experiments and methods new lead compounds with increased potency against APE1 activity are generated. The synthetic effort combined with the bioassay should provide SAR data, and will serve to rationalize the binding mode.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

REFERENCES

The following documents are cited herein.
1. Cereda S, Passoni P, Reni M, Vigano M G, Aldrighetti L, Nicoletti R, Villa E. The cisplatin, epirubicin, 5-fluorouracil, gemcitabine (PEFG) regimen in advanced biliary tract adenocarcinoma. Cancer 116: 2208-2214, 2010.
2. Eastman A. The formation, isolation, and characterization of DNA adducts produced by anticancer platinum complexes. Pharmacol. Ther. 37: 155-166, 1987.
3. Muggia F M. Cisplatin update. Semm. Oncol. 18: 1-4, 1991.
4. Cvitkovic E, Droz J P, Kaftan J, et al: Cisplatin, in Citkovic E, Droz J P, Armand J P, et al (eds): Handbook of Chemotherapy in Clinical Oncology (ed 2). Jersey, Channel Islands, Scientific Communication International, pp 242-245, 1993.
5. O'Dwyer P J, Johnson S W, Hamilton T C: Cisplatin and its analogues, in DeVita V T Jr, Hellman S, Rosenberg S A (eds): Cancer: Principals and Practice of Oncology. Philadelphia, Pa., Lippincott Raven, pp 418-432, 1997.
6. Wu F, Lin X, Okuda T, Howell S B. DNA polymerase zeta regulates cisplatin cytotoxicity, mutagenicity, and the rate of development of cisplatin resistance. Cancer Res. 64: 8029-8035, 2004.
7. Feghali J G, Liu W, Van De Water T R. L-n-acetylcysteine protection against cisplatin-induced auditory neuronal and hair cell toxicity. Laryngoscope 111: 1147-11455, 2001.
8. van den Berg J H, Beijnen J H, Balm A J, Schellens J H. Future opportunities in preventing cisplatin induced ototoxicity. Cancer Treat. Rev. 32: 390-397, 2006.
9. Zhang H, Mizumachi T, Carcel-Trullols J, Li L, Naito A, Spencer H J, Spring P M, Smoller B R, Watson A J, Margison G P, Higuchi M, Fan C Y. Targeting human 8-oxoguanine DNA glycosylase (hOGG1) to mitochondria enhances cisplatin cytotoxicity in hepatoma cells. Carcinogenesis 28: 1629-1637, 2007.
10. Izumi T, Wiederhold L R, Roy G, Roy R, Jaiswal A, Bhakat K K, Mitra S, Hazra T K. Mammalian DNA base excision repair proteins: their interactions and role in repair of oxidative DNA damage. Toxicology 193: 43-65, 2003.

11. Hazra T K, Das A, Das S, Choudhury S, Kow Y W, Roy R. Oxidative DNA damage repair in mammalian cells: a new perspective. DNA Repair (Amst). 6: 470-480, 2007.
12. Jiang Y, Guo C, Vasko M R, Kelley M R. Imlications of apurinic/apyrimidinic endonuclease in reactive oxygen signaling response after cisplatin treatment of dorsal root ganglion neurons. Cancer Res. 68: 6425-6434, 2008.
13. Al-Attar A, Gossage L, Fareed K R, Shehata M, Mohammed M, Zaitoun A M, Soomro I, Lobo D N, Abbotts R, Chan S, Madhusudan S. Human apurinic/apyrimidinic endonuclease (APE1) is a prognostic factor in ovarian, gastro-oesophageal and pancreatico-biliary cancers. Br. J. Cancer 102: 704-709, 2010.
14. Yang S, Irani K, Heffron S E, Jurnak F, Meyskens Jr F L. Alterations in the expression of the apurinic/apyrimidinic endonuclease-1/redox factor-1 (APE/Ref-1) in human melanoma and identification of the therapeutic potential of resveratrol as an APE/Ref-1 inhibitor. Mol. Cancer. Ther. 4: 1923-1935, 2005.
15. Wang D, Xiang D B, Yang X Q, Chen L S, Li M X, Zhong Z Y, Zhang Y S. APE1 overexpression is associated with cisplatin resistance in non-small cell lung cancer and targeted inhibition of APE1 enhances the activity of cisplatin in A549 cells. Lung Cancer 66: 298-304, 2009.
16. Wang D, Luo M, Kelley M R. Human apurinic endonuclease 1 (APE1) expression and prognostic significance in osteosarcoma: enhanced sensitivity of osteosarcoma to DNA damaging agents using silencing RNA APE1 expression inhibition. Mol. Cancer. Ther. 3: 679-686, 2004.
17. Koukourakis M I, Giatromanolaki A, Kakolyris S, Spyridis E, Georgoulias V, Funtzilas G, Hickson I D, Gatter K C, Harris A L. Nuclear expression of human apurinic/apyrimidinic endonuclease (HAP1/Ref-1) in head-and-neck cancer is associated with resistance to chemoradiotherapy and poor outcome. Int. J. Radiat. Oncol. Biol. Phys. 50: 27-36, 2001.
18. Zhang Y, Wang J, Xiang D, Wang D, Xin X. Alterations in the expression of the apurinic/apyrimidinic endonuclease-1/redox factor-1 (APE1/Ref-1) in human ovarian cancer and indentification of the therapeutic potential of APE1/Ref-1 inhibitor. Int. J. Oncol. 35: 1069-1079, 2009.
19. Jordan A, Reichard P. Ribonucleotide reductases. Annu. Rev. Biochem. 67: 71-98, 1998.
20. Kolberg M, Strand K R, Graff P, Andersson K K. Structure, function, and mechanism of ribonucleotide reductases. Biochim. Biophys. Acta 1699: 1-34, 2004.
21. Burris H A III, Moore M J, Andersen J, Green M R, Rothenberg M L, Modiano M R, et al. Improvements in survival and clinical benefit with gemcitabine as first-line therapy for patients with advanced pancreas cancer: a randomized trial. J. Clin. Oncol. 15: 2403-2413, 1997.
22. Viret F, Ychou M, Lepille D, Mineur L, Navarro F, Topart D, et al. Gemcitabine in combination with cisplatin (GP) versus gemcitabine (G) alone in the treatment of locally advanced or metastatic pancreatic cancer final results of a multicenter randomized phase II study. J. Clin. Oncol. 22(14S): abstract 4118, 2004.
23. Heinemann V, Quietzsch D, Gieseler F, Gonnermann M, Schoenekaes H, Rost A, et al. Randomized phase II trial of gemcitabine plus cisplatin compared with gemcitabine alone in advanced pancreatic cancer. J. Clin. Oncol. 24: 3946-3952, 2006.
24. Hidalgo M. Pancreatic cancer. N. Engl. J. Med. 362: 1605-1017, 2010.
25. Bardeesy N, DePinho R A. Pancreatic cancer biology and genetics. Nat. Rev. Cancer 2: 897-909, 2002.
26. Stathis A, Moore M J. Advanced pancreatic carcinoma: current treatment and future challenges. Nat. Rev. Clin. Oncol. 7: 163-172, 2010.
27. Manju K, Muralikrishna B, Parnaik V K. Expression of disease-causing lamin A mutants impairs the formation of DNA repair foci. J. Cell. Sci. 119: 2704-2714, 2006.
28. Kawai Y, Nakao T, Kunimura T, Kohda Y, Gemba M. Relationship of intracellular calcium and oxygen radicals to cisplatin-related renal cell injury. J. Pharmacol. Sci. 100: 65-72, 2006.
29. Kurihara N, Kubota T, Hoshiya Y, Otani Y, Ando N, Kumai K, Kitajima M. Phramacokinetics of cis-diamminedichloroplatinum (II) given as low-dose and high-dose infusions. J. Surg. Oncol. 62: 135-138, 1996.
30. Quasthoff S, Hartung H P. Chemotherapy-induced peripheral neuropathy. J. Neurol. 249: 9-17, 2002.
31. McDonald E S, Randon K R, Knight A, Windebank A J. Cisplatin preferentially binds to DNA in dorsal root ganglion neurons in vitro and in vivo: a potential mechanism for neurotoxicity. Neurobiol. Dis. 18: 305-313, 2005.
32. Tsang R Y, Al-Fayea T, Au H J. Cisplatin overdose: toxicities and management. Drug Saf. 32: 1109-1122, 2009.
33. Hansen S W. Gemcitabine in the treatment of ovarian cancer. Int. J. Gynecol. Cancer 11: 39-41, 2001.
34. Moufarij M A, Phillips D R, Cullinane C. Gemcitabine potentiates cisplatin cytotoxicity and inhibits repair of cispaltin-DNA damage in ovarian cancer cell lines. Mol. Pharmacol. 63: 862-869, 2003.
35. Van Moorsel C J, Pinedo H M, Bergman A M, Kuiper C M, Vermorken J B, van der Vijgh W J, Peters G J. Mechanisms of synergism between cisplatin and gemcitabine in ovarian and non-small cell lung cancer cell lines. Br. J. Cancer 80: 981-990, 1999.
36. Havaleshko D M, Cho H J, Conaway M, Owens C R, Hampton G, Lee J K, Theodorescu D. Prediction of drug combination chemosensitivity in human bladder cancer. Mol. Cancer. Ther. 6: 578-586, 2007.
37. Yoshizawa J, Takizawa A, Takeuchi O, Hiraku O, Sasaki K, Morimoto Y, Atsuda K, Inoue G, Suzuki Y, Asanuma F, Yamada Y. Experimental study of combination therapy with S-1 against pancreatic cancer. Cancer Chemother. Pharmacol. 64: 1211-1219, 2009.
38. Eichhorn M E, Ischenko I, Luedemann S, Strieth S, Papyan A, Werner A, Bohnenkamp H, Guenzi E, Preissler G, Michaelis U, Jauch K W, Bruns C J, Dellian M. Vascular targeting by EndoTAG-1 enhances therapeutic efficacy of conventional chemotherapy in lung and pancreatic cancer. Int. J. Cancer. 126: 1235-1245, 2010.
39. Louvet C, Labianca R, Hammel P, et al. Gemcitabine in combination with oxaliplatin compared with gemcitabine alone in locally advanced or metastatic pancreatic cancer: results of a GERCOR and GISCAD phase III trial. J. Clin. Oncol. 23: 3509-3516, 2005.
40. Hochster H S, Haller D G, de G A, et al. Consensus report of the international society of gastrointestinal oncology on therapeutic progress in advanced pancreatic cancer. Cancer 107: 676-685, 2006.
41. Xie D R, Liang H L, Wang Y, Guo S S, Yang Q. Meta-analysis on inoperable pancreatic cancer: a comparison between gemcitabine-based combination therapy and gemcitabine alone. World J. Gastroenterol. 12: 6973-6981, 2006.
42. Kleespies A, Ischenko I, Eichhorn M E, Seeliger H, Amendt C, Mantel!O, Jauch K W, Bruns C J. Matuzumab short-term therapy in experimental pancreatic cancer:

42. prolonged antitumor activity in combination with gemcitabine. Clin. Cancer Res. 14: 5426-5436, 2008.
43. Philip P A. Gemcitabine and platinum combinations in pancreatic cancer. Cancer 95: 908-911, 2002.
44. Tripathy D. Overview: gemcitabine as single-agent therapy for advanced breast cancer. Clin. Breast Cancer 3: 8-11, 2002.
45. Hoang T, Kim K, Jaslowski A, Koch P, Beatty P, McGovern J, et al. Phase II study of second-line gemcitabine in sensitive or refractory small cell lung cancer. Lung Cancer 42: 97-102, 2003.
46. Wu Y, Aravind S, Ranganathan G, Martin A, Nalysnyk L. Anemia and thrombocytopenia in patients undergoing chemotherapy for solid tumors: a descriptive study of a large outpatient oncology practice database, 2000-2007. Clin. Ther. 31: 2416-2432, 2009.
47. Dzagnidze A, Katsarava Z, Makhalova J, et al. Repair capacity for platinum-DNA adducts determines the severity of cisplatin-induced peripheral neuropathy. J. Neurosci. 27: 9451-9457, 2007.
48. Fung H and Demple B. A vital role for Ape1/Ref1 protein in repairing spontaneous DNA damage in human cells. Mol. Cell. 17: 463-470, 2005.
49. Sharma R A and Dianov G L. Targeting base excision repair to improve cancer therapies. Mol. Aspects. Med. 28: 345-374, 2007.
50. Mol C D, Izumi T, Mitra S, Tainer J A. DNA-bound structures and mutants reveal abasic DNA binding by APE1 and DNA repair coordination. Nature 403: 451-456, 2000.
51. Shao J, Zhou B, Chu B, Yen Y. Ribonucleotide reductase inhibitors and future drug design. Curr. Cancer Drug Targets 6: 409-431, 2006.
52. Tseng W C, Derse E, Cheng Y C, Brockman T W, Bennett L L. In vitro biological activity of 9-13-D-arabinofuranosyl-2-fluoroadenine and the biochemical actions of its triphosphate on DNA polymerases and ribonucleotide reductase from HeLa cells. Mol. Pharmacol. 21: 474-477, 1982.
53. Heinemann V, Xu Y Z, Chubb S, Sen A, Hertel L W, Grindey G B, Plunkett W. Inhibition of ribonucleotide reduction in CCRF-CEM cells by 2',2'-difluorodeoxycytidine. Mol. Pharmacol. 38: 567-572, 1990.
54. Yang L Y, Li L, Jiang H, Shen Y, Plunkett W. Expression of ERCC1 antisense RNA abrogates gemcitabine-mediated cytotoxic synergism with cisplatin in human colon tumor cells defective in mismatch repair but proficient in nucleotide excision repair. Clin. Cancer Res. 6: 773-778, 2000.
55. Rosa S, Fortini P, Karran P, Bignami M, Dogliotti E. Processing in vitro of an abasic site reacted with methoxyamine: a new assay for the detection of abasic sites formed in vivo. Nucleic Acids Res. 19: 5569-5574, 1991.
56. Horton J K, Wilson S H. Hypersensitivity phenotypes associated with genetic and synthetic inhibitor-induced base excision repair deficiency. DNA Repair (Amst) 6:530-543, 2007.
57. Taverna P, Liu L, Hwang H S, Hanson A J, Kinsella T J, Gerson S L. Methoxyamine potentiates DNA single strand breaks and double strand breaks induced by temozolomide in colon cancer cells. Mutat. Res. 485: 269-281, 2001.
58. Madhusudan S, Smart F, Shrimpton P, Parsons J L, Gardiner L, Houlbrook S, Talbot D C, Hammonds T, Freemont P A, Sternberg M J, Dianov G L, Hickson I D. Isolation of a small molecule inhibitor of DNA base excision repair. Nucleic Acids Res. 33: 4711-4724, 2005.
59. Seiple L A, Cardellina J H, Akee R, Stivers J T. Potent Inhibition of Human Ap Endonuclease I by Arylstibonic Acids. Mol. Pharmacol. 73: 669-677, 2008.
60. Simeonov A, Kulkarni A, Dorjsuren D, Jadhav A, Shen M, McNeill D R, Austin C P, Wilson D M. Identification and Characterization of Inhibitors of Human Apurinic/apyrimidinic Endonuclease APE1. PLoS ONE 4: e5740, 2009.
61. Zawahir Z, Dayam R, Deng J, Pereira C, Neamati N. Pharmacophore guided discovery of small-molecule human apurinic/apyrimidinic endonuclease 1 inhibitors. J. Med. Chem. 52: 20-32, 2009.
62. Bapat A, Glass L S, Luo M, Fishel M L, Long E C, Georgiadis M M, Kelley M R. Novel small molecule of Ape1 endonuclease blocks proliferation and reduces viability of glioblastoma cells. Pharmacol. Exp. Ther. 2010 May 26.
63. Burch P A, Ghosh C, Schroeder G, Allmer C, Woodhouse C L, Goldberg R M, Addo F, Bernath A M, Tschetter L K, Windschitl H E, Cobau C D. Phase II evaluation of continuous-infusion 5-fluorouracil, leucovorin, mitomycin-C, and oral dipyridamole in advanced measurable pancreatic cancer: a North Central Cancer Treatment Group Trial. Am. J. Clin. Oncol. 23: 534-537, 2000.
64. Reni M, Cereda S, Mazza E, Passoni P, Nicoletti R, Balzano G, Zerbi A, Arcidiacono P G, Staudacher C, Di Carlo V. PEFG (cisplatin, epirubicin, 5-fluorouracil, gemcitabine) regimen as second-line therapy in patients with progressive or recurrent pancreatic cancer after gemcitabine-containing chemotherapy. Am. J. Clin. Oncol. 31: 145-150, 2008.

What is claimed is:

1. A method for increasing cytotoxicity of a chemotherapeutic agent in a subject, the method comprising administering to the subject NSC-30049 or an analog thereof, an alkylating agent and an agent that binds to ribonucleotide reductase (RR) and reduces nucleotide synthesis relative to a reference;

wherein the analog is of formula:

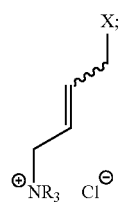

wherein X is F, Cl, Br, or OH; and

NR₃ is

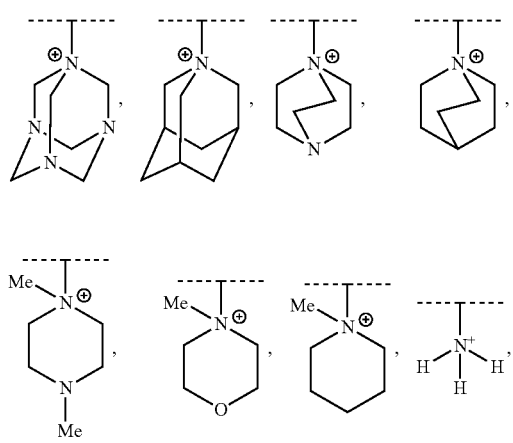

-continued

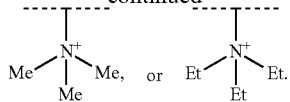

2. The method of claim 1, wherein NSC-30049 or an analog thereof and the alkylating agent are administered within about 7-14 days or are administered concurrently.

3. The method of claim 1, wherein NSC-30049 or an analog thereof and the alkylating agent are administered within about 3-5 days or are administered concurrently.

4. The method of claim 1, wherein the alkylating agent is cisplatin (CDDP).

5. The method of claim 1, wherein the agent that binds to ribonucleotide reductase (RR) and reduces nucleotide synthesis relative to a reference is gemcitabine (dFdC).

6. A method for increasing cytotoxicity of a chemotherapeutic agent in a subject, the method comprising administering to the subject NSC-30049, cisplatin (CDDP), and gemcitabine (dFdC).

* * * * *

SEQUENCE LISTING

<160> NUMBER OF SEQ ID NOS: 1

<210> SEQ ID NO 1
<211> LENGTH: 318
<212> TYPE: PRT
<213> ORGANISM: Homo sapiens

<400> SEQUENCE: 1

Met Pro Lys Arg Gly Lys Lys Gly Ala Val Ala Glu Asp Gly Asp Glu
1               5                   10                  15

Leu Arg Thr Glu Pro Glu Ala Lys Lys Ser Lys Thr Ala Ala Lys Lys
            20                  25                  30

```
Asn Asp Lys Glu Ala Ala Gly Glu Gly Pro Ala Leu Tyr Glu Asp Pro
    35                  40                  45
Pro Asp Gln Lys Thr Ser Pro Ser Gly Lys Pro Ala Thr Leu Lys Ile
    50                  55                  60
Cys Ser Trp Asn Val Asp Gly Leu Arg Ala Trp Ile Lys Lys Lys Gly
65              70                  75                  80
Leu Asp Trp Val Lys Glu Glu Ala Pro Asp Ile Leu Cys Leu Gln Glu
                85                  90                  95
Thr Lys Cys Ser Glu Asn Lys Leu Pro Ala Glu Leu Gln Glu Leu Pro
                100                 105                 110
Gly Leu Ser His Gln Tyr Trp Ser Ala Pro Ser Asp Lys Glu Gly Tyr
                115                 120                 125
Ser Gly Val Gly Leu Leu Ser Arg Gln Cys Pro Leu Lys Val Ser Tyr
    130                 135                 140
Gly Ile Gly Asp Glu Glu His Asp Gln Glu Gly Arg Val Ile Val Ala
145                 150                 155                 160
Glu Phe Asp Ser Phe Val Leu Val Thr Ala Tyr Val Pro Asn Ala Gly
                165                 170                 175
Arg Gly Leu Val Arg Leu Glu Tyr Arg Gln Arg Trp Asp Glu Ala Phe
                180                 185                 190
Arg Lys Phe Leu Lys Gly Leu Ala Ser Arg Lys Pro Leu Val Leu Cys
                195                 200                 205
Gly Asp Leu Asn Val Ala His Glu Glu Ile Asp Leu Arg Asn Pro Lys
    210                 215                 220
Gly Asn Lys Lys Asn Ala Gly Phe Thr Pro Gln Glu Arg Gln Gly Phe
225                 230                 235                 240
Gly Glu Leu Leu Gln Ala Val Pro Leu Ala Asp Ser Phe Arg His Leu
                245                 250                 255
Tyr Pro Asn Thr Pro Tyr Ala Tyr Thr Phe Trp Thr Tyr Met Met Asn
                260                 265                 270
Ala Arg Ser Lys Asn Val Gly Trp Arg Leu Asp Tyr Phe Leu Leu Ser
                275                 280                 285
His Ser Leu Leu Pro Ala Leu Cys Asp Ser Lys Ile Arg Ser Lys Ala
    290                 295                 300
Leu Gly Ser Asp His Cys Pro Ile Thr Leu Tyr Leu Ala Leu
305                 310                 315
```